United States Patent
Korth et al.

(10) Patent No.: US 7,501,534 B2
(45) Date of Patent: Mar. 10, 2009

(54) PROCESS FOR THE PREPARATION OF ORGANOSILANES

(75) Inventors: Karsten Korth, Grenzach-Wyhlen (DE); Philipp Albert, Lörrach (DE); Ingo Kiefer, Dossenbach-Schwörstadt (DE); Albert Frings, Brühl (DE); Louis Janssens, Merksem (BE); Horst Mertsch, Rheinfelden (DE)

(73) Assignee: Degussa AG, Düsseldorf (DE)

( * ) Notice: Subject to any disclaimer, the term of this patent is extended or adjusted under 35 U.S.C. 154(b) by 585 days.

(21) Appl. No.: 11/369,601

(22) Filed: Mar. 7, 2006

(65) Prior Publication Data

US 2006/0204422 A1 Sep. 14, 2006

(30) Foreign Application Priority Data

| Mar. 7, 2005 | (DE) | ................ 10 2005 010 294 |
| Jul. 12, 2005 | (DE) | ................ 10 2005 032 428 |
| Nov. 2, 2005 | (DE) | ................ 10 2005 052 233 |

(51) Int. Cl.
 *C07F 7/04* (2006.01)
(52) U.S. Cl. .................................... 556/427
(58) Field of Classification Search ............ 556/427
  See application file for complete search history.

(56) References Cited

U.S. PATENT DOCUMENTS

| 5,840,952 | A | 11/1998 | Kudo et al. | |
| 6,777,474 | B2 * | 8/2004 | Yanagisawa | 524/366 |
| 7,288,667 | B2 * | 10/2007 | Yanagisawa | 556/427 |
| 7,309,797 | B2 * | 12/2007 | Yanagisawa | 556/427 |
| 7,368,588 | B2 * | 5/2008 | Yanagisawa | 556/427 |
| 7,371,881 | B2 * | 5/2008 | Frings et al. | 556/427 |
| 2001/0037034 | A1 * | 11/2001 | Michel et al. | 556/427 |
| 2003/0176719 | A1 * | 9/2003 | Yanagisawa et al. | 556/427 |
| 2005/0124821 | A1 * | 6/2005 | Korth et al. | 556/427 |
| 2006/0052621 | A1 * | 3/2006 | Korth et al. | 556/427 |
| 2006/0094892 | A1 * | 5/2006 | Yanagisawa et al. | 556/400 |
| 2006/0161015 | A1 * | 7/2006 | Klockmann et al. | 556/427 |

FOREIGN PATENT DOCUMENTS

| DE | 196 51 849 A1 | 6/1998 |
| DE | 103 51 735 B3 | 12/2004 |
| EP | 0 471 164 A1 | 2/1992 |
| EP | 0 848 006 A | 4/1998 |
| EP | 0 949 263 A2 | 10/1999 |
| EP | 1 130 023 A2 | 9/2001 |
| GB | 1102251 | 2/1968 |

* cited by examiner

*Primary Examiner*—Porfirio Nazario Gonzalez
(74) *Attorney, Agent, or Firm*—Robert G. Weilacher; Smith, Gambrell & Russell

(57) ABSTRACT

A process for the preparation or organosilanes of the formula I

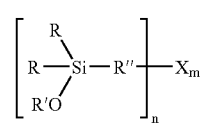

I by reacting a (haloorganyl)alkoxysilane of the formula II

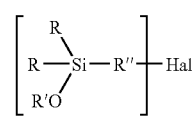

II with a sulphurization reagent selected from the group consisting or alkali metal hydrogen sulphide, alkali metal sulphide $Me_2S$, alkali metal polysulphide $Me_2S_g$ and any desired combinations thereof, and optionally additionally with sulphur and/or with $H_2S$, in an alcohol, the $Me_2S$ or $Me_2S_g$ containing more than 10% by weight of water and the alkali metal hydrogen sulphide containing more than 3% by weight of water.

9 Claims, No Drawings

PROCESS FOR THE PREPARATION OF ORGANOSILANES

INTRODUCTION AND BACKGROUND

The invention relates to a process for the preparation of organosilanes.

GB 1 102 251 discloses the reaction of anhydrous alkali metal hydrogen sulphides with (haloalkyl)alkoxysilanes in a methanolic medium to give the corresponding mercaptoalkyl) alkoxysilanes at atmospheric pressure. The unusually long reaction time (96 h) for achieving high conversions and the unsatisfactory yield achieved are disadvantageous in this procedure.

It is known that mercaptoalkyl)alkoxysilanes can be prepared by the reaction of anhydrous alkali metal hydrogen sulphide with suitable (haloalkyl)alkoxy-silanes in the presence of a 10-100% molar excess of $H_2S$ (U.S. Pat. No. 5,840, 952). Before the addition of the (haloalkyl)alkoxysilane, the alkali metal hydrogen sulphide is preferably formed by the reaction of alkali metal sulphide $Me_2S$ (Me—Li, Na, K) with $H_2S$ or by the reaction of $H_2S$ with alkali metal alcoholate. On the industrial scale, this process has the disadvantage that highly poisonous $H_2S$ has to be stored, metered and handled and the process is carried out in 2 stages, with the result that in principle the space-time yield of the process decreases.

It is furthermore. known that mercaptoalkyl) alkoxy-silanes can be prepared by reacting (haloalkyl)alkoxysilanes with anhydrous alkali metal hydrogen sulphide (NaSH) in polar, aprotic solvents (EP 0 471 164). The disadvantage of the process is that large amounts, at least 50% by volume, of solvent are used and this is toxic, for example in the case of dimethylformamide. In addition, the high boiling point of imethylformamide complicates the subsequent distillative working-up of the reaction products.

DE 103 517 35 discloses a process for the preparation of (mercaptoorganyl) alkoxysilanes, anhydrous, dried alkali metal hydrogen sulphide being reacted with a mixture of (haloorganyl) alkoxysilane and (haloorganyl)-halosilanes in an alcohol in a closed vessel in the absence of air and at an elevated pressure. The use of anhydrous alkali metal hydrogen sulphide is a disadvantage of this process.

EP 1130023 discloses the preparation of organosilylalkylpolysulphanes of the general formula $(R^1R^2R^3Si—R^4—)_2S_q$ from the organosilylalkyl halide of the general formula

$R^1R^2R^3Si—R^4—X$.

The reaction is carried out by initially introducing elemental sulphur and the organylalkyl halide in a polar organic solvent and adding anhydrous or virtually anhydrous ionic sulphide to the suspension. owing to the susceptibility of the Si-alkoxy bonds of the organosilylalkyl halide to hydrolysis, the ionic sulphides must be anhydrous or virtually anhydrous.

It is an object of the present invention to provide a process for the preparation of organosilanes which permits short reaction times in combination with good yields of crude product and in which water-containing sulphurization reagents can be used.

SUMMARY OF THE INVENTION

The invention relates to a process for the preparation of organosilanes of the general formula I

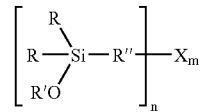

in which

R are identical or different and are a $C_1$-$C_8$-alkyl group, preferably $CH_3$ or $CH_2CH_3$, $C_7$-$C_8$-alkenyl, $C_1$-Cs-aryl or C1-$C_8$-aralkyl group or an OR' group, R' are identical or different and are a branched or straight-chain monovalent $C_1$-$C_{24}$—, preferably $C_1$-$C_4$— or $C_{12}$-$C_{18}$—, alkyl or alkenyl group, particularly preferably $CH_2CH_3$, an aryl group, an aralkyl group, a hydrogen (—H), an alkyl ether group O—$(CR^{111}_2)$—O-Alk or O—$(CR^{111}_2)$ y-O-Alk or an alkyl polyether group O—$(CR^{111}, O)$y-Alk or —O—$(CR^{111}_2$—$CR^{111}_2$—O) y-Alk, where y=2-20, preferably 2-10, particularly preferably 3-6, $R^{III}$, independently of one another, are H or an alkyl group, preferably a $CH_3$ group, and Alk is a branched or straight-chain, saturated or unsaturated, aliphatic, aromatic or mixed aliphatic/aromatic monovalent $C_1$-$C_{30}$—, preferably $C_2$-$C_{20}$-, particularly preferably $C_6$-$C_{18}$—, very particularly preferably $C_{10}$-$C_{18}$-, hydrocarbon group, R" is a branched or straight-chain, saturated or unsaturated, aliphatic, aromatic or mixed aliphatic/aromatic divalent $C_1$-$C_{30}$—, preferably $C_1$-$C_{20}$ particularly preferably $C_1$-$C_{10}$—, very particularly preferably $C_1$-$C_7$—, hydrocarbon group which is optionally substituted by F, Cl, Br, I, HS, $NH_2$ or NHR', X=S if n=2 and m is an average sulphur chain length of from 1.5 to 4.5, and X=SH if n=1 and m=1, by reacting a (haloorganyl)alkoxysilane of the formula II

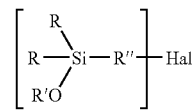

in which R, R' and R" have the above-mentioned meanings and Hal is chlorine, bromine, fluorine or iodine, with a sulphurization reagent selected from the group consisting of alkali metal hydrogen sulphide, metal sulphide $Me_2S$, metal polysulphide $Me_2S_g$ and any desired combinations thereof, where Me-alkali metal, $NH_4$ or (alkaline earth metal)$_{1/2}$, and g=1.5-8.0, and optionally additionally with sulphur and/or with $H_2S$ in alcohol, which is characterized in that the $Me_2S$ or $Me_2S_g$ contains more than 10% by weight, preferably more than 15% by weight, particularly preferably more than 20% by weight, very particularly preferably more than 30% by weight, of water and the alkali metal hydrogen sulphide contains more than 3% by weight, preferably more than 5% by weight, particularly preferably more than 10% by weight, very particularly preferably more than 12% by weight, exceedingly preferably more than 15% by weight, of water.

Surprisingly, it is found that the water present in the sulphurization reagents does not lead to complete hydrolysis and condensation of the alkoxysilanes, although basic reaction conditions are present and stoichiometrically more water is present than required in order to convert all SiOR bonds present into SiOH and subsequently, by condensation, into corresponding siloxanes containing Si—O—Si bonds.

DETAILED DESCRIPTION OF INVENTION

In the above formulae, R'' denotes, for example,
—$CH_2$—, —$CH_2CH_2$—, —$CH_2CH_2CH_2$—, —$CH_2CH_2CH_2CH_2$—, —$CH(CH_3)$—, —$CH_2CH(CH_3)$—, —$CH(CH_3)$ $CH_2$—, —$C(CH_3)_2$—, —$CH(C_2H_5)$—, —$CH_2CH_2CH(CH_3)$, —$CH_2CH(CH_3) CH_2$— or

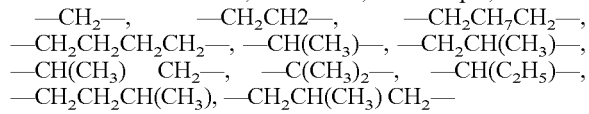

sulphur, $Me_2S_g$+sulphur, alkali metal hydrogen sulphide+$Me_2S_g$+$Me_2S$, $Me_2S_{g+Me2}S$, alkali metal hydrogen sulphide+$Me_2S$+sulphur, alkali metal hydrogen sulphide+$Me_2S_g$+sulphur, $Me_2S$+$Me_2S_g$+sulphur, alkali metal hydrogen sulphide+$Me_2S_g$+$Me_2S$+sulphur, $H_2S$+$Me_2S_g$+$Me_2S$+sulphur, $H_2S$+alkali metal hydrogen sulphide+$Me_2S_g$+$Me_2S$+sulphur, $H_2S$+alkali metal hydrogen sulphide+$Me_2S_g$+$Me_2S$, $H_2S$+alkali metal hydrogen sulphide+$Me_2S$, $H_2S$+alkali metal hydrogen sulphide+$Me_2S_g$, $H_2S$+$Me_2S$+sulphur, $H_2S$+$Me_2S_g$+sulphur, $H_2S$+$Me_2S_g$+$Me_2S$, $H_2S$+$Me_2S_g$ and $H_2S$+$Me_2S$.

Lithium hydrogen sulphide (LiSH), sodium hydrogen sulphide (NaSH), potassium hydrogen sulphide (KSH) and caesium hydrogen sulphide (CsSH) may be used as the alkali metal hydrogen sulphide.

$Li_2S$, $Na_2S$, $K_2S$, $Na_2S_2$, $Na_2S_3$, $Na_2S_4$, $K_2S_2$, $K_2S_3$, $K_2S_4$ or mixtures thereof may be used as the alkali metal sulphide $Me_2S$ or alkali metal polysulphide $Me_2S_g$.

The anhydrous sulphurization reagents may contain less than 60% by weight, preferably less than 50% by weight, particularly preferably less than 40% by weight, very particularly preferably less than 35% by weight, of water.

The anhydrous sulphurization reagents may contain between 10 and 60% by weight, preferably between 10 and 50% by weight, particularly preferably between 15 and 50% by weight, of water.

The water content of the sulphurization reagents is determined as follows: for the determination of the water content, glass beads are breathed upon, covered with phosphorus pentoxide and then introduced into a U-tube. About 3 g of the sample are weighed into a 50 ml flask, heated for 2 hours at 320° C. under a nitrogen stream (30 ml/min) dried with Sicapent, and then allowed to stand for a further 30 min under a nitrogen stream. The moist carrier gas is passed via a tube connection from the flask into the U-tube. Possible condensations between flask and U-tube are expelled during the heat-up phase with the aid of a hot air blower. The U-tube is reweighed and the amount of water liberated from the sulphurization reagents is determined gravimetrically.

Compounds of the general formula I or mixtures of compounds of the general formula I may form in the process according to the invention for the preparation of organosilanes.

The compounds of the general formula I which form in the process according to the invention or the mixtures of compounds of the general formula I may have water contents of less than 3% by weight, preferably less than 2% by weight, particularly preferably less than 1% by weight, very particularly preferably less than 0.5% by weight, measured according to DIN ENISO 12937, including an iodometric back-titration in order to distinguish between $H_2O$ and NS species ($H_2S$ etc.).

The alkyl polyether group in formulae I and II may contain ethylene oxide ($CH_2$—$CH_2$—O) and propylene oxide units, for example ($CH(CH_3)$—$CH_2$—O) or ($CH_2$—$CH(CH_3)$—O).

The alkyl polyether group O—$(CR^{III}_2O)_y$-Alk or O—$(CR^{III}_2$—$CR^{III}_2O)_y$-Alk may be O—$(CH_2$—$CH_2O)_2$—$C_8H_{17}$, O—$(CH_2$—$CH_2O)_3$—$C_8H_{17}$, O—$(CH_2$—$CH_2O)_4$—$C_8H_{17}$, O—$(CH_2$—$CH_2O)_5$—$C_8H_{17}$, O—$(CH_2$—$CH_2O)_6$—$C_8H_{17}$, O—$(CH_2$—$CH_2O)_7$—$C_8H_{17}$, O—$(CH(CH_3)$—$CH_2O)_2$—$C_8H_{17}$, O—$(CH(CH_3)$—$CH_2O)_3$—$C_8H_{17}$, O—$(CH(CH_3)$—$CH_2O)_4$—$C_8H_{17}$, O—$(CH(CH_3)$—$CH_2O)_5$—$C_8H_{17}$, O—$(CH(CH_3)$—$CH_2O)_6$—$C_8H_{17}$, O—$(CH(CH_3)$—$CH_2O)_7$—$C_8H_{17}$, O—$(CH_2$—$CH_2O)_2$—$C_9H_{19}$, O—$(CH_2$—$CH_2O)_3$—$C_9H_{19}$, O—$(CH_2$—$CH_2O)_4$—$C_9H_{19}$, O—$(CH_2$—$CH_2O)_5$—$C_9H_{19}$, O—$(CH_2$—$CH_2O)_6$—$C_9H_{19}$, O—$(CH_2$—$CH_2O)_7$—$C_9H_{19}$, O—$(CH(CH_3)$—$CH_2O)_2$—$C_9H_{19}$, O—$(CH(CH_3)$—$CH_2O)_3$—$C_9H_{19}$, O—$(CH(CH_3)$—$CH_2O)_4$—$C_9H_{19}$, O—$(CH(CH_3)$—$CH_2O)_5$—$C_9H_{19}$, O—$(CH(CH_3)$—$CH_2O)_6$—$C_9H_{19}$, O—$(CH(CH_3)$—$CH_2O)_7$—$C_9H_{19}$, O—$(CH_2$—$CH_2O)_2$—$C_{10}H_{21}$, O—$(CH_2$—$CH_2O)_3$—$C_{10}H_{21}$, O—$(CH_2$—$CH_2O)_4$—$C_{10}H_{21}$, O—$(CH_2$—$CH_2O)_5$—$C_{10}H_{21}$, O—$(CH_2$—$CH_2O)_6$—$C_{10}H_{21}$, O—$(CH_2$—$CH_2O)_7$—$C_{10}H_{21}$, O—$(CH(CH_3)$—$CH_2O)_2$—$C_{10}H_{21}$, O—$(CH(CH_3)$—$CH_2O)_3$—$C_{10}H_{21}$, O—$(CH(CH_3)$—$CH_2O)_4$—$C_{10}H_{21}$, O—$(CH(CH_3)$—$CH_2O)_5$—$C_{10}H_{21}$, O—$(CH(CH_3)$—$CH_2O)_6$—$C_{10}H_{21}$, O—$(CH(CH_3)$—$CH_2O)_7$—$C_{10}H_{21}$, O—$(CH_2$—$CH_2O)_2$—$C_{11}H_{23}$, O—$(C_2$—$CH_2O)_3$—$C_{11}H_{23}$, O—$(CH_2$—$CH_2O)_4$—$C_{11}H_{23}$, O—$(CH_2$—$CH_2O)_5$—$C_{1123}$, O—$(CH_2$—$CH_2O)_6$—$C_{11}H_{23}$, O—$(CH_2$—$CH_2O)_7$—$C_{11}H_{23}$, O—$(CH(CH_3)$—$CH_2O)_2$—$C_{11}H_{23}$, O—$(CH(CH_3)$—$CH_2O)_3$—$C_{11}H_{23}$, O—$(CH(CH_3)$—$CH_2O)_4$—$C_{11}H_{23}$, O—$(CH(CH_3)$—$CH_2O)_5$—$C_{11}H_{23}$, O—$(CH(CH_3)$—$CH_2O)_6$—$C_{11}H_{23}$, O—$(CH(CH_3)$—$CH_2O)_7$—$C_{11}H_{23}$, O—$(CH_2$—$CH_2O)_2$—$C_{12}H_{25}$, O—$(CH_2$—$CH_2O)_3$—$C_{12}H_{25}$, O—$(CH_2$—$CH_2O)_4$—$C_{12}H_{25}$, O—$(CH_2$—$CH_2O)_5$—$C_{12}H_{25}$, O—$(CH_2$—$CH_2O)_6$—$C_{12}H_{25}$, O—$(CH_2$—$CH_2O)_7$—$C_{12}H_{25}$, O—$(CH(CH_3)$—$CH_2O)_2$—$C_{12}H_{25}$, O—$(CH(CH_3)$—$CH_2O)_3$—$C_{12}H_{25}$, O—$(CH(CH_3)$—$CH_2O)_4$—$C_{12}H_{25}$, O—$(CH(CH_3)$—$CH_2O)_5$—$C_{12}H_{25}$, O—$(CH(CH_3)$—$CH_2O)_6$—$C_{12}H_{25}$, O—$(CH(CH_3)$—$CH_2O)_7$—$C_{12}H_{25}$, O—$(CH_2$—$CH_2O)_2$—$C_{13}H_{27}$, O—$(CH_2$—$CH_2O)_3$—$C_{13}H_{27}$, O—$(CH_2$—$CH_2O)_4$—$C_{13}H_{27}$, O—$(CH_2$—$CH_2O)_5$—$C_{13}H_{27}$, O—$(CH_2$—$CH_2O)_6$—$C_{13}H_{27}$, O—$(CH_2$—$CH_2O)_7$—$C_{13}H_{27}$, O—$(CH(CH_3)$—$CH_2O)_2$—$C_{13}H_{27}$, O—$(CH(CH_3)$—$CH_2O)_3$—$C_{13}H_{27}$, O—$(CH(CH_3)$—$CH_2O)_4$—$C_{13}H_{27}$, O—$(CH(CH_3)$—$CH_2O)_5$—$C_{13}H_{27}$, O—$(CH(CH_3)$—$CH_2O)_6$—$C_{13}H_{27}$, O—$(CH(CH_3)$—$CH_2O)_7$—$C_{13}H_{27}$, O—$(CH_2$—$CH_2O)_2$—$C_{14}H_{29}$, O—$(CH_2$—$CH_2O)_3$—$C_{14}H_{29}$, O—$(CH_2$—$CH_2O)_4$—$C_{14}H_{29}$, O—$(CH_2$—$CH_2O)_5$—$C_{14}H_{29}$, O—$(CH_2$—$CH_2O)_6$—$C_{14}H_{29}$, O—$(CH_2$—$CH_2O)_7$—$C_{14}H_{29}$, O—$(CH(CH_3)$—$CH_2O)_2$—$C_{14}H_{29}$, O—$(CH(CH_3)$—$CH_2O)_3$—$C_{14}H_{29}$, O—$(CH(CH_3)$—$CH_2O)_4$—$C_{14}H_{29}$, O—$(CH(CH_3)$—$CH_2O)_5$—$C_{14}H_{29}$, O—$(CH(CH_3)$—$CH_2)_6$—$C_{14}H_{29}$, O—$(CH(CH_3)$—$CH_2O)_7$—$C_{14}H_{29}$, O—($CH_2$—$CH_2O$)$_2$—$C_{15}H_{31}$, O—($CH_2$—$CH_2O$)$_3$—$C_{15}H_{31}$, O—($CH_2$—$CH_2O$)$_4$—$C_{15}H_{31}$, O—($CH_2$—$CH_2O$)$_5$—$C_{15}H_{31}$, O—($CH_2$—$CH_2O$)$_6$—$C_{15}H_{31}$, O—($CH_2$—$CH_2O$)$_7$—$C_{15}H_{31}$,
O—($CH(CH_3)$—$CH_2O$)$_2$—$C_{15}H_{31}$, O—($CH(CH_3)$—$CH_2O$)$_3$—$C_{15}H_{31}$, O—($CH(CH_3)$—$CH_2O$)$_4$—$C_{15}H_{31}$, O—($CH(CH_3)$—$CH_2O$)$_5$—$C_{15}H_{31}$, O—($CH(CH_3)$—$CH_2O$)$_6$—$C_{15}H_{31}$, O—($CH(CH_3)$—$CH_2O$)$_7$—$C_{15}H_{31}$,
O—($CH_2$—$CH_2O$)$_2$—$C_{16}H_{33}$, O—($CH_2$—$CH_2O$)$_3$—$C_{16}H_{33}$, O—($CH_2$—$CH_2O$)$_4$—$C_{16}H_{33}$, O—($CH_2$—$CH_2O$)$_5$—$C_{16}H_{33}$, O—($CH_2$—$CH_2O$)$_6$—$C_{16}H_{33}$, O—($CH_2$—$CH_2O$)$_7$—$C_{16}H_{33}$,
O—($CH(CH_3)$—$CH_2O$)—$C_{16}H_{33}$, O—($CH(CH_3)$—$CH_2O$)$_3$—$C_{16}H_{33}$, O—($CH(CH_3)$—$CH_2O$)$_4$—$C_{16}H_{33}$, O—($CH(CH_3)$—$CH_2O$)$_5$—$C_{16}H_{33}$, O—($CH(CH_3)$—$CH_2O$)$_6$—$C_{16}H_{33}$ or O—($CH(CH_3)$—$CH_2O$)$_7$—$C_{16}H_{33}$.

(Haloorganyl)alkoxysilanes of the formula II which can preferably be used are
3-chlorobutyl(triethoxysilane),
3-chlorobutyl(trimethoxysilane),
3-chlorobutyl(diethoxymethoxysilane),
3-chloropropyl(triethoxysilane),
3-chloropropyl(trimethoxysilane),
3-chloropropyl(diethoxymethoxysilane),
2-chloroethyl(triethoxysilane),
2-chloroethyl(trimethoxyslaone),
2-chloroethyl(diethoxymethoxysilane),
1-chloromethyl(triethoxysilane),
1-chloromethyl(trimethoxysilane),
1-chloromethyl(diethoxymethoxysilane),
3-chloropropyl(diethoxymethylsilane),
3-chloropropyl(dimethoxymethylsilane),
2-chloroethyl(dliethoxymethylsilane),
2-chloroethyl(dimethoxyethylsilane),
1-chloromethyl(diethoxymethylsilane),
1-chloromethyl(dimethoxymethylsilane),
3-chloropropyl(ethoxydimethylsilane),
3-chloropropyl(methoxydimethylsilane),
2-chloroethyl(ethoxydimethylsilane),
2-chloroethyl(methoxydirmethylsilane),
1-chloromethyl(ethoxydimethylsilane),
1-chloromethyl(methoxydimethylsilane),
[($C_9H_{19}O$—($CH_2$—$CH_2O$)$_2$](MeO)$_2$Si($CH_2$)$_3$Cl,
[($C_9H_{19}O$—($CH_2$—$CH_2O$)$_3$](MeO)$_2$Si($CH_2$)$_3$Cl,
[($C_9H_{19}O$—($CH_2$—$CH_2O$)$_4$](MeO)$_2$Si($CH_2$)$_3$Cl,
[($C_9H_{19}O$—($CH_2$—$CH_2O$)$_5$](MeO)$_2$Si($CH_2$)$_3$Cl,
[($C_9H_{19}O$—($CH_2$—$CH_2O$)$_6$](MeO)$_2$Si($CH_2$)$_3$Cl,
[($C_{12}H_{25}O$—($CH_2$—$CH_2O$)$_2$](MeO)$_2$Si($CH_2$)$_3$Cl,
[($C_{12}H_{25}O$—($CH_2$—$CH_2O$)$_3$](MeO)$_2$Si($CH_2$)$_3$Cl,
[($C_{12}H_{25}O$—($CH_2$—$CH_2O$)$_4$](MeO)$_2$Si($CH_2$)$_3$Cl,
[($C_{12}H_{25}O$—($CH_2$—$CH_2O$)$_5$](MeO)$_2$Si($CH_2$)$_3$Cl,
[($C_{12}H_{25}O$—($CH_2$—$CH_2O$)$_6$](MeO)$_2$Si($CH_2$)$_3$Cl,
[($C_{13}H_{27}O$—($CH_2$—$CH_2O$)$_2$](MeO)$_2$Si($CH_2$)$_3$Cl,
[($C_{13}H_{27}O$—($CH_2$—$CH_2O$)$_3$](MeO)$_2$Si($CH_2$)$_3$Cl,
[($C_{13}H_{27}O$—($CH_2$—$CH_2O$)$_4$](MeO)$_2$Si($CH_2$)$_3$Cl,
[($C_{13}H_{27}O$—($CH_2$—$CH_2O$)$_5$](MeO)$_2$Si($CH_2$)$_3$Cl,
[($C_{13}H_{27}O$—($CH_2$—$CH_2O$)$_6$](MeO)$_2$Si($CH_2$)$_3$Cl,
[($C_{14}H_{29}O$—($CH_2$—$CH_2O$)$_2$](MeO)$_2$Si($CH_2$)$_3$Cl,
[($C_{14}H_{29}O$—($CH_2$—$CH_2O$)$_3$](MeO)$_2$Si($CH_2$)$_3$Cl,
[($C_{14}H_{29}O$—($CH_2$—$CH_2O$)$_4$](MeO)$_2$Si($CH_2$)$_3$Cl,
[($C_{14}H_{29}O$—($CH_2$—$CH_2O$)$_5$](MeO)$_2$Si($CH_2$)$_3$Cl,
[($C_{14}H_{29}O$—($CH_2$—$CH_2O$)$_6$](MeO)$_2$Si($CH_2$)$_3$Cl,
[($C_9H_{19}O$—($CH_2$—$CH_2O$)$_2$]$_2$(MeO)Si($CH_2$)$_3$Cl,
[($C_9H_{19}O$—($CH_2$—$CH_2O$)$_3$]$_2$(MeO)Si($CH_2$)$_3$Cl,
[($C_9H_{19}O$—($CH_2$—$CH_2O$)$_4$]$_2$(MeO)Si($CH_2$)$_3$Cl,
[($C_9H_{19}O$—($CH_2$—$CH_2O$)$_5$]$_2$(MeO)Si($CH_2$)$_3$Cl,
[($C_9H_{19}O$—($CH_2$—$CH_2O$)$_6$]$_2$(MeO)Si($CH_2$)$_3$Cl,
[($C_{12}H_{25}O$—($CH_2$—$CH_2O$)$_2$]$_2$(MeO)Si($CH_2$)$_3$Cl,
[($C_{12}H_{25}O$—($CH_2$—$CH_2O$)$_3$]$_2$(MeO)Si($CH_2$)$_3$Cl,
[($C_{12}H_{25}O$—($CH_2$—$CH_2O$)$_4$]$_2$(MeO)Si($CH_2$)$_3$Cl,
[($C_{12}H_{25}O$—($CH_2$—$CH_2O$)$_5$]$_2$(MeO)Si($CH_2$)$_3$Cl,
[($C_{12}H_{25}O$—($CH_2$—$CH_2O$)$_6$]$_2$(MeO)Si($CH_2$)$_3$Cl,
[($C_{13}H_{27}O$—($CH_2$—$CH_2O$)$_2$]$_2$(MeO)Si($CH_2$)$_3$Cl,
[($C_{13}H_{27}O$—($CH_2$—$CH_2O$)$_3$]$_2$(MeO)Si($CH_2$)$_3$Cl,
[($C_{13}H_{27}O$—($CH_2$—$CH_2O$)$_4$]$_2$(MeO)Si($CH_2$)$_3$Cl,
[($C_{13}H_{27}O$—($CH_2$—$CH_2O$)$_5$]$_2$(MeO)Si($CH_2$)$_3$Cl,
[($C_{13}H_{27}O$—($CH_2$—$CH_2O$)$_6$]$_2$(MeO)Si($CH_2$)$_3$Cl,
[($C_{14}H_{29}O$—($CH_2$—$CH_2O$)$_2$]$_2$(MeO)Si($CH_2$)$_3$Cl,
[($C_{14}H_{29}O$—($CH_2$—$CH_2O$)$_3$]$_2$(MeO)Si($CH_2$)$_3$Cl,
[($C_{14}H_{29}O$—($CH_2$—$CH_2O$)$_4$]$_2$(MeO)Si($CH_2$)$_3$Cl,
[($C_{14}H_{29}O$—($CH_2$—$CH_2O$)$_5$]$_2$(MeO)Si($CH_2$)$_3$Cl,
[($C_{14}H_{29}O$—($CH_2$—$CH_2O$)$_6$]$_2$(MeO)Si($CH_2$)$_3$Cl,
[($C_9H_{19}O$—($CH_2$—$CH_2O$)$_2$](EtO)$_2$Si($CH_2$)$_3$Cl,
[($C_9H_{19}O$—($CH_2$—$CH_2O$)$_3$](EtO)$_2$Si($CH_2$)$_3$Cl,
[($C_9H_{19}O$—($CH_2$—$CH_2O$)$_4$](EtO)$_2$Si($CH_2$)$_3$Cl,
[($C_9H_{19}O$—($CH_2$—$CH_2O$)$_5$](EtO)$_2$Si($CH_2$)$_3$Cl,
[($C_9H_{19}O$—($CH_2$—$CH_2O$)$_6$](EtO)$_2$Si($CH_2$)$_3$Cl,
[($C_{12}H_{25}O$—($CH_2$—$CH_2O$)$_2$](EtO)$_2$Si($CH_2$)$_3$Cl,
[($C_{12}H_{25}O$—($CH_2$—$CH_2O$)$_3$](EtO)$_2$Si($CH_2$)$_3$Cl,
[($C_{12}H_{25}O$—($CH_2$—$CH_2O$)$_4$](EtO)$_2$Si($CH_2$)$_3$Cl,
[($C_{12}H_{25}O$—($CH_2$—$CH_2O$)$_5$](EtO)$_2$Si($CH_2$)$_3$Cl,
[($C_{12}H_{25}O$—($CH_2$—$CH_2O$)$_6$](EtO)$_2$Si($CH_2$)$_3$Cl,
[($C_{13}H_{27}O$—($CH_2$—$CH_2O$)$_2$](EtO)$_2$Si($CH_2$)$_3$Cl,
[($C_{13}H_{27}O$—($CH_2$—$CH_2O$)$_3$](EtO)$_2$Si($CH_2$)$_3$Cl,
[($C_{13}H_{27}O$—($CH_2$—$CH_2O$)$_4$](EtO)$_2$Si($CH_2$)$_3$Cl,
[($C_{13}H_{27}O$—($CH_2$—$CH_2O$)$_5$](EtO)$_2$Si($CH_2$)$_3$Cl,
[($C_{13}H_{27}O$—($CH_2$—$CH_2O$)$_6$](EtO)$_2$Si($CH_2$)$_3$Cl,
[($C_{14}H_{29}O$—($CH_2$—$CH_2O$)$_2$](EtO)$_2$Si($CH_2$)$_3$Cl,
[($C_{14}H_{29}O$—($CH_2$—$CH_2O$)$_3$](EtO)$_2$Si($CH_2$)$_3$Cl,
[($C_{14}H_{29}O$—($CH_2$—$CH_2O$)$_4$](EtO)$_2$Si($CH_2$)$_3$Cl,
[($C_{13}H_{29}O$—($CH_2$—$CH_2O$)$_5$](EtO)$_2$Si($CH_2$)$_3$Cl,
[($C_{14}H_{29}O$—($CH_2$—$CH_2O$)$_6$](EtO)$_2$Si($CH_2$)$_3$Cl,
[($C_9H_{19}O$—($CH_2$—$CH_2O$)$_2$]$_2$(EtO)Si($CH_2$)$_3$Cl,
[($C_9H_{19}O$—($CH_2$—$CH_2O$)$_3$]$_2$(EtO)Si($CH_2$)$_3$Cl,
[($C_9H_{19}O$—($CH_2$—$CH_2O$)$_4$]$_2$(EtO)Si($CH_2$)$_3$Cl,
[($C_9H_{19}O$—($CH_2$—$CH_2O$)$_5$]$_2$(EtO)Si($CH_2$)$_3$Cl,
[($C_9H_{19}O$—($CH_2$—$CH_2O$)$_6$]$_2$(EtO)Si($CH_2$)$_3$Cl,
[($C_{12}H_{25}O$—($CH_2$—$CH_2O$)$_2$]$_2$(EtO)Si($CH_2$)$_3$Cl,
[($C_{12}H_{25}O$—($CH_2$—$CH_2O$)$_3$]$_2$(EtO)Si($CH_2$)$_3$Cl,
[($C_{12}H_{25}O$—($CH_2$—$CH_2O$)$_4$]$_2$(EtO)Si($CH_2$)$_3$Cl,
[($C_{12}H_{25}O$—($CH_2$—$CH_2O$)$_5$]$_2$(EtO)Si($CH_2$)$_3$Cl,
[($C_{12}H_{25}O$—($CH_2$—$CH_2O$)$_6$]$_2$(EtO)Si($CH_2$)$_3$Cl,
[($C_{13}H_{27}O$—($CH_2$—$CH_2O$)$_2$]$_2$(EtO)Si($CH_2$)$_3$Cl,
[($C_{13}H_{27}O$—($CH_2$—$CH_2O$)$_3$]$_2$(EtO)Si($CH_2$)$_3$Cl,
[($C_{13}H_{27}O$—($CH_2$—$CH_2O$)$_4$]$_2$(EtO)Si($CH_2$)$_3$Cl,
[($C_{13}H_{27}O$—($CH_2$—$CH_2O$)$_5$]$_2$(EtO)Si($CH_2$)$_3$Cl,
[($C_{13}H_{27}O$—($CH_2$—$CH_2O$)$_6$]$_2$(EtO)Si($CH_2$)$_3$Cl,
[($C_{14}H_{29}O$—($CH_2$—$CH_2O$)$_2$]$_2$(EtO)Si($CH_2$)$_3$Cl,
[($C_{14}H_{29}O$—($CH_2$—$CH_2O$)$_3$]$_2$(EtO)Si($CH_2$)$_3$Cl,
[($C_{14}H_{29}O$—($CH_2$—$CH_2O$)$_4$]$_2$(EtO)Si($CH_2$)$_3$Cl,
[($C_{14}H_{29}O$—($CH_2$—$CH_2O$)$_5$]$_2$(EtO)Si($CH_2$)$_3$Cl,
[($C_{14}H_{29}O$—($CH_2$—$CH_2O$)$_6$]$_2$(EtO)Si($CH_2$)$_3$Cl,
[($C_9H_{19}O$—($CH_2$—$CH_2O$)$_2$]$_3$Si($CH_2$)$_3$Cl,
[($C_9H_{19}O$—($CH_2$—$CH_2O$)$_3$]$_3$Si($CH_2$)$_3$Cl,
[($C_9H_{19}O$—($CH_2$—$CH_2O$)$_4$]$_3$Si($CH_2$)$_3$Cl,
[($C_9H_{19}O$—($CH_2$—$CH_2O$)$_5$]$_3$Si($CH_2$)$_3$Cl,
[($C_9H_{19}O$—($CH_2$—$CH_2O$)$_6$]$_3$Si($CH_2$)$_3$Cl,
[($C_{12}H_{25}O$—($CH_2$—$CH_2O$)$_2$]$_3$Si($CH_2$)$_3$Cl,
[($C_{12}H_{25}O$—($CH_2$—$CH_2O$)$_3$]$_3$Si($CH_2$)$_3$Cl,
[($C_{12}H_{25}O$—($CH_2$—$CH_2O$)$_4$]$_3$Si($CH_2$)$_3$Cl,
[($C_{12}H_{25}O$—($CH_2$—$CH_2O$)$_5$]$_3$Si($CH_2$)$_3$Cl,
[($C_{12}H_{25}O$—($CH_2$—$CH_2O$)$_6$]$_3$Si($CH_2$)$_3$Cl,
[($C_{13}H_{27}O$—($CH_2$—$CH_2O$)$_2$]$_3$Si($CH_2$)$_3$Cl,
[($C_{13}H_{27}O$—($CH_2$—$CH_2O$)$_3$]$_3$Si($CH_2$)$_3$Cl,

[(C₁₃H₂₇O—(CH₂—CH₂O)₄]₃Si(CH₂)₃Cl,
[(C₁₃H₂₇O—(CH₂—CH₂O)₅]₃Si(CH₂)₃Cl,
[(C₁₃H₂₇O—(CH₂—CH₂O)₆]₃Si(CH₂)₃Cl,
[(C₁₄H₂₉O—(CH₂—CH₂O)₂]₃Si(CH₂)₃Cl,
[(C₁₄H₂₉O—(CH₂—CH₂O)₃]₃Si(CH₂)₃Cl,
[(C₁₄H₂₉O—(CH₂—CH₂O)₄]₃Si(CH₂)₃Cl,
[(C₁₄H₂₉O—(CH₂—CH₂O)₅]₃Si(CH₂)₃Cl or
[(C₁₄H₂₉O—(CH₂—CH₂O)₆]₃Si(CH₂)₃Cl.

The (haloorganyl)alkoxysilane may be a (haloorganyl)alkoxysilane of the formula II or a mixture of (haloorganyl)alkoxysilanes of the formula II.

Additives may be added before, during or after the reaction.

Additives may be non-alcoholic solvents. Alkanes, such as, for example, pentane, hexane, cyclohexane, heptane or octane, ether, such as, for example, diethyl ether, tetrahycrofuran, 1,2-dimethoxyethane, dioxane, dioxolane, ethylene glycols or propylene glycols, aromatic solvents, such as, for example, benzene, toluene, o-xylene, m-xylene or p-xylene, or carbonyl-containing solvents, such as, for example, dimethylformamide, can preferably be used, in pure or technical-grade quality, as additives which are non-alcoholic solvents.

At the beginning of the reaction and/or during the reaction and/or the end of the reaction, polar, protic, aprotic, basic or acidic additives can be added to the reaction mixture.

Additives may be, for example, $H_2S$, (alkali metal ion) $H_2PO_4$, (alkali metal ion)$_2HPO_4$, (alkali metal ion)$_3PO_4$, (alkali metal ion)$HCO_3$, (alkali metal ion)$_2CO_3$, (alkali metal ion)$_2SO_4$ or (alkali metal ion)$HSO_4$, $KH_2PO_4$, $K_2HPO_4$, $KHCO_3$, $NaHCO_3$, $K_2CO_3$ or $Na_2CO_3$ can preferably be used.

The yield of crude product of the process according to the invention may be greater than 80%, preferably greater than 85%, particularly preferably greater than 90%, very particularly preferably greater than 95%, based on the theoretical yield with respect to the amount of (haloorganyl)alkoxysilane used.

The yield of crude product may be the gravimetrically determined sum of all liquid compounds isolated after solvent and solids have been removed.

The (haloorganyl)alkoxysilane, additives and alcohol can be mixed with one another in any desired sequence or manner at any desired temperature and in any desired duration and only thereafter the sulphurization reagent added.

The (haloorganyl)alkoxysilane, additives and the sulphurization reagent can be mixed with one another in any desired sequence or manner, at any desired temperature and in any desired duration and only thereafter the alcohol added.

The sulphurization reagent, additives and the alcohol can be mixed with one another in any desired sequence or manner, at any desired temperature and in any desired duration and only thereafter the (haloorganyl)-alkoxysilane added.

The (haloorganyl)alkoxysilane, alcohol and the sulphurization reagent can be mixed with one another in any desired sequence or manner, at any desired temperature and in any desired duration and only thereafter additives added.

The water-containing sulphurization reagents used can be added to the reaction as solids or in solution.

The sulphurization reagents required for the reaction can be formed before or during the reaction from sulphur-containing compounds.

The sulphurization reagents required for the reaction can be formed before or during the reaction from metal hydroxides+sulphur, metal hydroxides+alkali metal hydrogen sulphides, metal hydroxides+sulphur+alkali metal hydrogen sulphides, metal hydroxides+$H_2S$+sulphur+alkali metal hydrogen sulphides or metal hydroxides+$H_2S$+sulphur+alkali metal sulphides.

The sulphurization reagents required for the reaction can be formed before or during the reaction from alcoholates+sulphur, alcoholates+$H_2S$+sulphur or alcoholates+alkali metal hydrogen sulphides+sulphur.

The sulphur-containing compounds can react completely or incompletely, reversibly or irreversibly to give alkali metal hydrogen sulphides or $H_2S$ under the reaction conditions by protonation.

The sulphur-containing compounds can react completely or incompletely, reversibly or irreversibly to give alkali metal sulphides or alkali metal hydrogen sulphides under the reaction conditions by deprotonation.

The protonation of the sulphur compounds from which alkali metal hydrogen sulphides are formed before or during the reaction can take place by means of $H_2S$ and/or organic and/or inorganic acids.

The deprotonation of the sulphur compounds from which alkali metal sulphides are formed before or during the reaction can take place by means of organic and/or inorganic bases.

The deprotonation of $H_2S$, resulting in the formation of alkali metal hydrogen sulphides before or during the reaction, can take place by means of organic and/or inorganic bases.

The water-containing sulphurization reagents may contain more than 30% by weight, preferably more than 40% by weight, particularly preferably more than 50% by weight, very particularly preferably more than 60% by weight, of sulphurization reagents.

In addition to water, the water-containing sulphurization reagents may contain further secondary constituents in an amount of less than 50% by weight, preferably less than 30% by weight, particularly preferably less than 20% by weight, very particularly preferably less than 10% by weight.

Further secondary constituents of water-containing sulphurization reagents in addition to water may be, independently of one another, alkali metal carbonates, alkali metal bicarbonates, alkali metal hydroxides, alkali metal sulphates, alkali metal hydrogen sulphates, alkali metal thiosulphates and/or alkali metal hydrogen thiosulphates.

The molar amount of sulphurization reagents used may exceed the sum of the molar amounts of the (haloorganyl) alkoxysilane used by from 1 mol % to 50 mol %, preferably by from 5 to 30 mol %, particularly preferably by from 5 to 20 mol %, very particularly preferably by from 5 to 10 mol %.

Amounts of sulphurization reagents smaller than the stoichiometrically required amounts can lead to incomplete conversion. Consequently, either the product may subsequently be contaminated with starting material or a complicated purification may be necessary in order to separate starting materials and products from one another.

Primary, secondary or tertiary alcohols having 1 to 24, preferably 1 to 6, particularly preferably 1 to 4, carbon atoms can be used as the alcohol.

Alkyl ethers of the formula HO—(CR$^{IV}_2$)—O-Alk or HO—(CR$^{IV}_2$)$_y$—O-Alk or alkyl polyethers of the formula HO—(CR$^{IV}_2$O)$_y$-Alk or HO—(CR$^{IV}_2$—CR$^{IV}_2$—O)$_y$-Alk, where y=2-20, preferably 2-10, particularly preferably 3-6, R$^{IV}$, independently of one another, are H or an alkyl group, preferably CH$_3$ group, and Alk is a branched or straight-chain, saturated or unsaturated, aliphatic, aromatic or mixed aliphatic/aromatic monovalent C$_1$-C$_{30}$—, preferably C$_2$-C$_{20}$—, particularly preferably C$_6$-C$_{18}$—, very particularly preferably C$_{10}$-C$_{18}$—, hydrocarbon group, can be used as the alcohol.

Primary, secondary or tertiary alcohols which may be used are methanol, ethanol, n-propanol, i-propanol, i-butanol, n-butanol, dodecanol, tetradecanol, hexadecanol or octadecanol. Alkyl polyethers which may be used are HO—($CH_2$—$CH_2$—O)$_a$—$C_bH_{2b+1}$, where a is from 2 to 20, preferably 2-10, particularly preferably 2-8, very particularly preferably 3-6 and b=1-30, preferably 2-20, particularly preferably 6-18. very particularly preferably 10-18.

Primary alcohols may be
HO—($CH_2$—$CH_2$—O)$_2$—$C_6H_{13}$, HO—($CH_2$—$CH_2$—O)$_3$—$C_6H_{13}$, HO—($CH_2$—$CH_2$—O)$_4$—$C_6H_{13}$, HO—($CH_2$—$CH_2$—O)$_5$—$C_6H_{13}$, HO—($CH_2$—$CH_2$—O)$_6$—$C_6H_{13}$, HO—($CH_2$—$CH_2$—O)$_7$—$C_6H_{13}$, HO—($CH_2$—$CH_2$—O)$_8$—$C_6H_{13}$, HO—($CH_2$—$CH_2$—O)$_9$—$C_6H_{13}$,
HO—($CH_2$—$CH_2$—O)$_2$—$C_{10}H_{21}$, HO—($CH_2$—$CH_2$—O)$_3$—$C_{10}H_{21}$, HO—($CH_2$—$CH_2$—O)$_4$—$C_{10}H_{21}$, HO—($CH_2$—$CH_2$—O)$_5$—$C_{10}H_{21}$, HO—($CH_2$—$CH_2$—O)$_6$—$C_{10}H_{21}$, HO—($CH_2$—$CH_2$—O)$_7$—$C_{10}H_{21}$, HO—($CH_2$—$CH_2$—O)$_8$—$C_{10}H_{21}$, HO—($CH_2$—$CH_2$—O)$_9$—$C_{10}H_{21}$,
HO—($CH_2$—$CH_2$—O)$_2$—$C_{13}H_{27}$, HO—($CH_2$—$CH_2$—O)$_3$—$C_{13}H_{27}$, HO—($CH_2$—$CH_2$—O)$_4$—$C_{13}H_{27}$, HO—($CH_2$—$CH_2$—O)$_5$—$C_{13}H_{27}$, HO—($CH_2$—$CH_2$—O)$_6$—$C_{13}H_{27}$, HO—($CH_2$—$CH_2$—O)$_7$—$C_{13}H_{27}$, HO—($CH_2$—$CH_2$—O)$_8$—$C_{13}H_{27}$, HO—($CH_2$—$CH_2$—O)$_9$—$C_{13}H_{27}$,
HO—($CH_2$—$CH_2$—O)$_2$—$C_{15}H_{31}$, HO—($CH_2$—$CH_2$—O)$_3$—$C_{15}H_{31}$, HO—($CH_2$—$CH_2$—O)$_4$—$C_{15}H_{31}$, HO—($CH_2$—$CH_2$—O)$_5$—$C_{15}H_{31}$, HO—($CH_2$—$CH_2$—O)$_6$—$C_{15}H_{31}$, HO—($CH_2$—$CH_2$—O)$_7$—$C_{15}H_{31}$, HO—($CH_2$—$CH_2$—O)$_8$—$C_{15}H_{31}$ or HO—($CH_2$—$CH_2$—O)$_9$—$C_{15}H_{31}$.

The amount of alcohol may be at least 0.1% by volume, preferably from 10 to 800% by volume, particularly preferably from 50 to 700% by volume, very particularly preferably from 100 to 500% by volume, of the silane components used.

The alcohol may contain less than 20% by weight, preferably less than 10% by weight, particularly preferably less than 5% by weight, especially preferably less than 1% by weight, very particularly preferably less than 0.1% by weight, of water.

Mixtures of alcohols may be used as the alcohol.

The reaction can be effected at temperatures between 0 and 180° C., preferably between 70 and 150° C., particularly preferably between 70 and 125° C.

During the working-up of the crude products, the alcoholic solvents can be removed in vacuo and at elevated temperature. water-entraining substances (azeotrope formers) known to the person skilled in the art may be added and used in order to separate off not only the solvent but also water in vacuo at elevated temperature. The water present in the crude product can be removed in vacuo at elevated temperature from the crude product or the end product. Auxiliaries and apparatuses known to the person skilled in the art can be used for separating off solvent, azeotrope former and water.

Vertical tube evaporators, horizontal tube evaporators, inclined evaporators, falling-film evaporators, plate-type evaporators, blowpipe evaporators, rotor evaporators, centrifugal evaporators, screw evaporators, thin-film evaporators and thin-film strippers can preferably be used.

The reaction can be effected in reaction vessels or autoclaves which are corrosion-resistant or susceptible to corrosion.

The reaction can preferably be effected in corrosion-resistant reaction vessels or autoclaves, for example of glass, Teflon, enameled or coated steel, Hastelloy or tantalum.

The solvent/water mixture can be removed from the crude product suspension, preferably at reduced pressure, and the resulting suspension, containing the resulting organosilane of the general formula I, can be separated from the solid, preferably by centrifuging, decanting or filtration.

The solvent/water mixture can be removed at a pressure of from 800 mbar to 10 mbar, preferably by distillation. The solvent/water mixture may contain ethanol.

The resulting suspension may contain Me(Hal), for example NaCl, buffer salts and organosilanes of the general formula I.

The solvent can be removed from the crude product suspension, the mixture containing the organosilanes of the general formula (I) and the solid Me(Hal) can be mixed with water containing at least one buffer, and the phases forming can be separated.

The working-up of the crude product suspension may include filtration and separation of solid constituents. The working-up of the crude product suspension may include a distillation and separation of volatile constituents. The working-up of the crude product suspension may include first a distillation and then a filtration. The working-up of the crude product suspension may include first a filtration and then a distillation. The working-up of the crude product suspension may include first a filtration, then a distillation and thereafter a further filtration.

The salt-containing crude product suspension present after the reaction can be worked up at atmospheric pressure or reduced pressure, preferably at a reduced pressure between 1 and 700 mbar, particularly preferably between 5 and 500 mbar, very particularly preferably between 10 and 250 mbar.

The salt-containing product suspension present after the reaction can be worked up at ambient temperature or elevated temperature, preferably between 20 and 200° C., particularly preferably between 40 and 150° C., very particularly preferably between 50 and 100° C.

A mixture of product and solid may form during the working-up. A mixture of product and alcohol may form during the working-up. A mixture of product, alcohol and water may form during the working-up. A mixture of product and water may form during the working-up. A mixture of product, solid and water may form during the working-up. A mixture of product, Me(Hal), for example sodium chloride, and water may form during the working-up. A mixture of product, Me(Hal), for example sodium chloride, alcohol and water may form during the working-up.

Water may be added to a mixture of product and/or solid and/or alcohol and/or water.

Water may be added in an amount of from 1 to 200% by weight, preferably 1 to 100% by weight, particularly preferably 5 to 75% by weight, very particularly preferably 5 to 50% by weight, based on the product.

The water may be demineralized water. The water may contain a buffer, for example sodium bicarbonate or sodium carbonate. The buffer content of the water may be 1% by weight—20% by weight, preferably 2% by weight—5% by weight.

The added water may have a pH of between 3 and 11, preferably between 4 and 10, particularly preferably between 5 and 9, very particularly preferably between 7 and 9.

The pH of the added water can be adjusted by the buffer, for example $NaHCO_3$.

The solid can preferably be present in the aqueous phase. The salt Me(Hal), for example sodium chloride, can preferably be present in the aqueous phase.

The product may separate from the salt-containing aqueous phase by phase separation. After the phase separation the product can be separated from the salt-containing aqueous phase. After the salt-containing phase has been separated off, the product can be dried.

In a first preferred embodiment for the preparation of organosilanes of the general formula I, where X=SH, m=1 and n=1, an alkali metal hydrogen sulphide may be used as the water-containing sulphurization reagent.

In this first embodiment, additives selected from the group consisting H$_2$S, CO$_2$, (haloorganyl)halosilane or a compound which is capable of donating a proton reversibly or irreversibly to alkali metal alcoholates in the pH range between 5 and 9 can be added to the reaction mixture before, during or after the reaction.

Compounds which, in combination with alcohols, liberate organic or inorganic acids can be added as additives in the preparation of organosilanes of the general formula I, where X=SH, before, during and/or at the end of the reaction.

In the preparation of organosilanes of the general formula I, where X=SH, the amount of alcohol may be at least 10% by volume, preferably from 10 to 800% by volume, particularly preferably from 50 to 500% by volume, very particularly preferably from 100 to 300% by volume, of the silane components used.

Compounds which liberate inorganic acids in the presence of alcohols may be chlorosilanes. Chlorosilanes may contain from 1 to 4 Si—Cl bonds per silicon atom. Chlorosilanes may be (CH$_3$)SiCl$_3$, (CH$_3$)$_2$SiCl$_2$, (CH$_3$)$_3$SiCl, SiCl$_4$, HSiCl$_3$ or H$_2$SiCl$_2$.

Compounds which are capable of donating a proton reversibly or irreversibly to alkali metal alcqholates in the pH range between 5 and 9 may be, for example, organic or inorganic acids.

Organic acids may be compounds of the following parent structures: alkyl-COOH, aryl-COOH, aralkyl-COOH, alkyl-S(O)$_2$OH, HOOC-alkylene-COOH, HOOC-aryl-COOH or HOOC-aralkyl-COOH.

Organic acids may be, for example, formic acid, acetic acid, propanoic acid, pivalic acid, isooctanoic acid, isononanoic acid, lauric acid (C12), myristic acid (C14), palmitic acid (C16), stearic acid (C18), oleic acid, linoleic acid, linolenic acid, benzoic acid, oxalic acid, 1,4-cyclohexanedicarboxylic acid, adipic acid, 1,12-dodecanedioic acid, aminoundecanoic acid, phthalic acid, terephthalic acid, maleic acid, fumaric acid, malonic acid, acrylic acid or methacrylic acid.

Inorganic acids may be, for example, compounds of the composition HCl, H$_2$SO$_4$, H$_3$PO$_4$, (alkali metal ion)H$_2$PO$_4$, (alkali metal ion)$_2$HPO$_4$, H$_2$CO$_3$, (alkali metal ion)HCO$_3$, or (alkali metal ion)HSO$_4$. Compounds of the structure (alkali metal ion)H$_2$PO$_4$ can preferably be KH$_2$PO$_4$ and NaH$_2$PO$_4$. Compounds of the structure (alkali metal ion)$_2$HPO$_4$ can preferably be K$_2$HPO$_4$ and Na$_2$HPO$_4$. Compounds of the structure (alkali metal ion)HCO$_3$ can preferably be KHCO$_3$ and NaHCO$_3$. Compounds of the structure (alkali metal ion)HSO$_4$ can preferably be KHSO$_4$ and NaRSO$_4$. The inorganic acid H$_2$CO$_3$ can be obtained by passing CO$_2$ into the water-containing reaction mixture.

Acidic or basic additives which are added to the reaction mixture before, during or at the end of the process may have the structure (alkali metal ion)H$_2$PO$_4$, (alkali metal ion)(OH), (alkali metal ion)$_2$HPO$_4$, (alkali metal ion)$_3$PO$_4$, (alkali metal ion)HCO$_3$, (alkali metal ion)$_2$CO$_3$, (alkali metal ion)$_2$SO$_4$ or (alkali metal ion)HSO$_4$. Compounds of the structure (alkali metal ion)H$_2$PO$_4$ can preferably be KH$_2$PO$_4$ and NaH$_2$PO$_4$. Compounds of the structure (alkali metal ion)$_2$HPO$_4$ can preferably be K$_2$HPO$_4$ and Na$_2$HPO$_4$. Compounds of the structure (alkali metal ion)HCO$_3$ can preferably be KHCO$_3$ and NaHCO$_3$. Compounds of the structure (alkali metal ion)HSO$_4$ can preferably be KHSO$_4$ and NaHSO$_4$.

The reaction for the preparation of organosilanes of the general formula I where X=SH can preferably be carried out under elevated pressure (>0.5 bar gauge pressure). The elevated pressure may be between 20 and 0.5 bar, preferably between 15 and 0.5 bar, particularly preferably from 10 to 0.5 bar, very particularly preferably from 5 to 0.5 bar, gauge pressure.

The reaction for the preparation of organosilanes of the general formula I where X=SH can preferably be carried out in a closed vessel and optionally under an inert gas.

The reaction for the preparation of organosilanes of the general formula I where X=SH can preferably be carried out in the absence of air.

The reaction for the preparation of organosilanes of the general formula I where X=SH can preferably be carried out in such a way that the gas forming cannot escape from the reaction space.

Organosilanes of the general formula I may be:
3-mercaptopropyl(trimethoxysilane),
3-mercaptopropyl(dimethoxyhydroxysilane),
3-mercaptopropyl(triethoxysilane),
3-mercaptopropyl(diethoxyhydroxysilane),
3-mercaptopropyl(diethoxymethoxysilane),
3-mercaptopropyl(tripropoxysilane),
3-mercaptopropyl(dipropoxymethoxysilane),
3-mercaptopropyl(dipropoxyhydroxysilane),
3-mercaptopropyl(tridodecanoxysilane),
3-marcaptopropyl(didodecanoxyhydroxysilane),
3-mercaptopropyl(tritetradecanoxysilane),
3-mercaptopropyl(trihexadecanoxysilane),
3-mercaptopropyl(trioctadecanoxysilane),
3-mercaptopropyl(didodecanoxy)tetradecanoxysilane,
3-mercaptopropyl(dodecanoxy)tetradecanoxy(hexadecanoxy) silane,
3-mercaptopropyl(dimethoxymethylsilane),
3-mercaptopropyl(methoxymethylhydroxysilane),
3-mercaptopropyl(methoxydimethylsilane),
3-mercaptopropyl(hydroxydimethylsilane),
3-mercaptopropyl(diethoxymethylsilane),
3-mercaptopropyl(ethoxyhydroxymethylsilane),
3-mercaptopropyl(ethoxydimethylsilane),
3-mercaptopropyl(dipropoxymethylsilane),
3-mercaptopropyl(propoxymethylhydroxysilane),
3-mercaptopropyl(propoxydimethylsilane),
3-mercaptopropyl(diisopropoxymethylsilane),
3-mercaptopropyl(isopropoxydimethylsilane),
3-mercaptopropyl(dibutoxymethylsilane),
3-mercaptopropyl(butoxydimethylsilane),
3-mercaptopropyl(diisobutoxymethylsilane),
3-mercaptopropyl(isobutoxymethylhydroxysilane),
3-mercaptopropyl(isobutoxydimethylsilane),
3-mercaptopropyl(didodecanoxymethylsilane),
3-marcaptopropyl(dodecanoxydimethylsilane),
3-mercaptopropyl(ditetradecanoxymethylsilane),
3-mercaptopropyl(tetradecanoxymethylhydroxysilane),
3-mercaptopropyl(tetradecanoxydimethylsilane),
2-mercaptoethyl(trimethoxysilane),
2-mercaptoethyl(triethoxysilane),
2-mercaptoethyl(diethoxymethoxysilane),
2-mercaptoethyl(tripropoxysilane),
2-mercaptoethyl(dipropoxymethoxysilane),
2-mercaptoethyl(tridodecanoxysilane),
2-mercaptoethyl(tritetradecanoxysilane),
2-mercaptoethyl(trihexadecanoxysilane),
2-mercaptoethyl(trioctadecanoxysilane),
2-mercaptoethyl(didodecanoxy)tetradecanoxysilane, 2-mercaptoethyl(dodecanoxy)tetradecanoxy(hexadecanoxy)-silane,
2-mercaptoethyl(dimethoxymethylsilane),
2-mercaptoethyl(methoxymethylhydroxysilane),
2-mercaptoethyl(methoxydimethylsilane),
2-mercaptoethyl(diethoxymethylsilane),
2-mercaptoethyl(ethoxydimethylsilane),
2-mercaptoethyl(hydroxydimethylsilane),
1-mercaptomethyl(trimethoxysilane),
1-mercaptomethyl(triethoxysilane),
1-mercaptomethyl(diethoxymethoxysilane),
1-mercaptomethyl(diethoxyhydroxysilane),
1-mercaptomethyl(dipropoxymethoxysilane),
1-mercaptomethyl(tripropoxysilane),
1-mercaptomethyl(trimethoxysilane),
1-mercaptomethyl(dimethoxymethylsilane),
1-marcaptomethyl methoxydimethylsilane),
1-mercaptomethyl(diethoxymethylsilane),
1-mercaptomethyl(ethoxymethylhydroxysilane),
1-mercaptomethyl(ethoxydimethylsilane),
1,3-dimercaptopropyl(trimethoxysilane),
1,3-dimercaptopropyl(triethoxysilane),
1,3-dimercaptopropyl(tripropoxysilane),
1,3-dimercaptopropyl(tridodecanoxysilane),
1,3-dimercaptopropyl(tritetradecanoxysilane),
1,3-dimercaptopropyl(trihexadecanoxysilane),
2,3-dimercaptopropyl(trimethoxysilane),
2,3-dimercaptopropyl(triethoxysilane),
2,3-dimercaptopropyl(tripropoxysilane),
2,3-dimercaptopropyl(tridodecanoxysilane),
2,3-dimercaptopropyl(tritetradecanoxysilane),
2,3-dimercaptopropyl(trihexadecanoxysilane),
3-mercaptobutyl(trimethoxysilane),
3-mercaptobutyl(triethoxysilane),
3-mercaptobutyl(diethoxymethoxysilane),
3-mercaptobutyl(tripropoxysilane),
3-mercaptobutyl(dipropoxymethoxysilane),
3-mercaptobutyl(dimethoxymethylsilane),
3-mercaptobutyl(diethoxymethylsilane),
3-mercaptobutyl(dimethylmethoxysilane),
3-mercaptobutyl(dimethylethoxysilane),
3-mercaptobutyl(dimethylhydroxysilane),
3-mercaptobutyl(tridodecanoxysilane),
3-mercaptobutyl(tritetradecanoxysilane),
3-mercaptobutyl(trihexadecanoxysilane),
3-mercaptobutyl(didodecanoxy)tetradecanoxyailane,
3-mercaptobutyl(dodecanoxy)tetradecanoxy(hexadecanoxy)-silane,
3-mercapto-2-methyl-propyl(trimethoxysilane),
3-mercapto-2-methyl-propyl(triethoxysilane),
3-mercapto-2-methyl-propyl(diethoxymethoxysilane),
3-mercapto-2-methyl-propyl(tripropoxysilane),
3-mercapto-2-methyl-propyl(dipropoxymethoxysilane),
3-mercapto-2-methyl-propyl(tridodecanoxysilane),
3-mercapto-2-methyl-propyl(tritetradecanoxysilane),
3-mercapto-2-methyl-propyl(trihexadecanoxysilane),
3-mercapto-2-methyl-propyl(trioctadecanoxysilane),
3-mercapto-2-methyl-propyl(didodecanoxy)-tetradecanoxysilane,
3-mercapto-2-methyl-propyl(dodecanoxy)-tetradecanoxy(hexadecanoxy)silane,
3-mercapto-2-methyl-propyl(dimethoxymethylsilane),
3-mercapto-2-methyl-propyl(methoxydimethylsilane),
3-mercapto-2-methyl-propyl(diethoxymethylsilane),
3-mercapto-2-methyl-propyl(ethoxydimethylsilane),
3-mercapto-2-methyl-propyl(hydroxydimethylsilane),
3-mercapto-2-methyl-propyl(dipropoxymethylsilane),
3-mercapto-2-methyl-propyl(propoxydimethylsilane),
3-mercapto-2-methyl-propyl(diisopropoxymethylsilane),
3-mercapto-2-methyl-propyl(isopropoxydimethylsilane),
3-mercapto-2-methyl-propyl(dibutoxymethylsilane),
3-mercapto-2-methyl-propyl(butoxydimethylsilane),
3-mercapto-2-methyl-propyl(diisobutoxymethylsilane),
3-mercapto-2-methyl-propyl(isobutoxydimethylsilane),
3-mercapto-2-methyl-propyl(didodecanoxymethylsilane),
3-mercapto-2-methyl-propyl(dodecanoxydimethylsilane),
3-mercapto-2-methyl-propyl(ditetradecanoxymethylsilane),
3-mercapto-2-methyl-propyl(tetradecanoxydimethylsilane),
$[(C_9H_{19}O-(CH_2-CH_2O)_2](MeO)_2Si(CH_2)_3SH$,
$[(C_9H_{19}O-(CH_2-CH_2O)_3](MeO)_2Si(CH_2)_3SH$,
$[(C_9H_{19}O-(CH_2-CH_2O)_4](MeO)_2Si(CH_2)_3SH$,
$[(C_9H_{19}O-(CH_2-CH_2O)_5](MeO)_2Si(CH_2)_3SH$,
$[(C_9H_{19}O-(CH_2-CH_2O)_6](MeO)_2Si(CH_2)_3SH$,
$[(C_{12}H_{25}O-(CH_2-CH_2O)_2](MeO)_2Si(CH_2)_3SH$,
$[(C_{12}H_{25}O-(CH_2-CH_2O)_3](MeO)_2Si(CH_2)_3SH$,
$[(C_{12}H_{25}O-(CH_2-CH_2O)_4](MeO)_2Si(CH_2)_3SH$,
$[(C_{12}H_{25}O-(CH_2-CH_2O)_5](MeO)_2Si(CH_2)_3SH$,
$[(C_{12}H_{25}O-(CH_2-CH_2O)_6](MeO)_2Si(CH_2)_3SH$,
$[(C_{13}H_{27}O-(CH_2-CH_2O)_2](MeO)_2Si(CH_2)_3SH$,
$[(C_{13}H_{27}O-(CH_2-CH_2O)_3](MeO)_2Si(CH_2)_3SH$,
$[(C_{13}H_{27}O-(CH_2-CH_2O)_4](MeO)_2Si(CH_2)_3SH$,
$[(C_{13}H_{27}O-(CH_2-CH_2O)_5](MeO)_2Si(CH_2)_3SH$,
$[(C_{13}H_{27}O-(CH_2-CH_2O)_6](MeO)_2Si(CH_2)_3SH$,
$[(C_{14}H_{29}O-(CH_2-CH_2O)_2](MeO)_2Si(CH_2)_3SH$,
$[(C_{14}H_{29}O-(CH_2-CH_2O)_3](MeO)_2Si(CH_2)_3SH$,
$[(C_{14}H_{29}O-(CH_2-CH_2O)_4](MeO)_2Si(CH_2)_3SH$,
$[(C_{14}H_{29}O-(CH_2-CH_2O)_5](MeO)_2Si(CH_2)_3SH$,
$[(C_{14}H_{29}O-(CH_2-CH_2O)_6](MeO)_2Si(CH_2)_3SH$,
$[(C_9H_{19}O-(CH_2-CH_2O)_2]_2(MeO)Si(CH_2)_3SH$,
$[(C_9H_{19}O-(CH_2-CH_2O)_3]_2(MeO)Si(CH_2)_3SH$,
$[(C_9H_{19}O-(CH_2-CH_2O)_4]_2(MeO)Si(CH_2)_3SH$,
$[(C_9H_{19}O-(CH_2-CH_2O)_5]_2(MeO)Si(CH_2)_3SH$,
$[(C_9H_{19}O-(CH_2-CH_2O)_6]_2(MeO)Si(CH_2)_3SH$,
$[(C_{12}H_{25}O-(CH_2-CH_2O)_2]_2(MeO)Si(CH_2)_3SH$,
$[(C_{12}H_{25}O-(CH_2-CH_2O)_3]_2(MeO)Si(CH_2)_3SH$,
$[(C_{12}H_{25}O-(CH_2-CH_2O)_4]_2(MeO)Si(CH_2)_3SH$,
$[(C_{12}H_{25}O-(CH_2-CH_2O)_5]_2(MeO)Si(CH_2)_3SH$,
$[(C_{12}H_{25}O-(CH_2-CH_2O)_6]_2(MeO)Si(CH_2)_3SH$,
$[(C_{13}H_{27}O-(CH_2-CH_2O)_2]_2(MeO)Si(CH_2)_3SH$,
$[(C_{13}H_{27}O-(CH_2-CH_2O)_3]_2(MeO)Si(CH_2)_3SH$,
$[(C_{13}H_{27}O-(CH_2-CH_2O)_4]_2(MeO)Si(CH_2)_3SH$,
$[(C_{13}H_{27}O-(CH_2-CH_2O)_5]_2(MeO)Si(CH_2)_3SH$,
$[(C_{13}H_{27}O-(CH_2-CH_2O)_6]_2(MeO)Si(CH_2)_3SH$,
$[(C_{14}H_{29}O-(CH_2-CH_2O)_2]_2(MeO)Si(CH_2)_3SH$,
$[(C_{14}H_{29}O-(CH_2-CH_2O)_3]_2(MeO)Si(CH_2)_3SH$,
$[(C_{14}H_{29}O-(CH_2-CH_2O)_4]_2(MeO)Si(CH_2)_3SH$,
$[(C_{14}H_{29}O-(CH_2-CH_2O)_5]_2(MeO)Si(CH_2)_3SH$,
$[(C_{14}H_{29}O-(CH_2-CH_2O)_6]_2(MeO)Si(CH_2)_3SH$,
$[(C_9H_{19}O-(CH_2-CH_2O)_2](EtO)_2Si(CH_2)_3SH$,
$[(C_9H_{19}O-(CH_2-CH_2O)_3](EtO)_2Si(CH_2)_3SH$,
$[(C_9H_{19}O-(CH_2-CH_2O)_4](EtO)_2Si(CH_2)_3SH$,
$[(C_9H_{19}O-(CH_2-CH_2O)_5](EtO)_2Si(CH_2)_3SH$,
$[(C_9H_{19}O-(CH_2-CH_2O)_6](EtO)_2Si(CH_2)_3SH$,
$[(C_{12}H_{25}O-(CH_2-CH_2O)_2](EtO)_2Si(CH_2)_3SH$,
$[(C_{12}H_{25}O-(CH_2-CH_2O)_3](EtO)_2Si(CH_2)_3SH$,
$[(C_{12}H_{25}O-(CH_2-CH_2O)_4](EtO)_2Si(CH_2)_3SH$,
$[(C_{12}H_{25}O-(CH_2-CH_2O)_5](EtO)_2Si(CH_2)_3SH$,
$[(C_{12}H_{25}O-(CH_2-CH_2O)_6](EtO)_2Si(CH_2)_3SH$,
$[(C_{13}H_{27}O-(CH_2-CH_2O)_2](EtO)_2Si(CH_2)_3SH$,
$[(C_{13}H_{27}O-(CH_2-CH_2O)_3](EtO)_2Si(CH_2)_3SH$,
$[(C_{13}H_{27}O-(CH_2-CH_2O)_4](EtO)_2Si(CH_2)_3SH$,
$[(C_{13}H_{27}O-(CH_2-CH_2O)_5](EtO)_2Si(CH_2)_3SH$,
$[(C_{13}H_{27}O-(CH_2-CH_2O)_6](EtO)_2Si(CH_2)_3SH$,
$[(C_{14}H_{29}O-(CH_2-CH_2O)_2](EtO)_2Si(CH_2)_3SH$,

[(C$_{14}$H$_{29}$O—(CH$_2$—CH$_2$O)$_3$](EtO)$_2$Si(CH$_2$)$_3$SH,
[(C$_{14}$H$_{29}$O—(CH$_2$—CH$_2$O)$_4$](EtO)$_2$Si(CH$_2$)$_3$SH,
[(C$_{14}$H$_{29}$O—(CH$_2$—CH$_2$O)$_5$](EtO)$_2$Si(CH$_2$)$_3$SH,
[(C$_{14}$H$_{29}$O—(CH$_2$—CH$_2$O)$_6$](EtO)$_2$Si(CH$_2$)$_3$SH,
[(C$_9$H$_{19}$O—(CH$_2$—CH$_2$O)$_2$]$_2$(EtO)Si(CH$_2$)$_3$SH,
[(C$_9$H$_{19}$O—(CH$_2$—CH$_2$O)$_3$]$_2$(EtO)Si(CH$_2$)$_3$SH,
[(C$_9$H$_{19}$O—(CH$_2$—CH$_2$O)$_4$]$_2$(EtO)Si(CH$_2$)$_3$SH,
[(C$_9$H$_{19}$O—(CH$_2$—CH$_2$O)$_5$]$_2$(EtO)Si(CH$_2$)$_3$SH,
[(C$_9$H$_{19}$O—(CH$_2$—CH$_2$O)$_6$]$_2$(EtO)Si(CH$_2$)$_3$SH,
[(C$_{12}$H$_{25}$O—(CH$_2$—CH$_2$O)$_2$]$_2$(EtO)Si(CH$_2$)$_3$SH,
[(C$_{12}$H$_{25}$O—(CH$_2$—CH$_2$O)$_3$]$_2$(EtO)Si(CH$_2$)$_3$SH,
[(C$_{12}$H$_{25}$O—(CH$_2$—CH$_2$O)$_4$]$_2$(EtO)Si(CH$_2$)$_3$SH,
[(C$_{12}$H$_{25}$O—(CH$_2$—CH$_2$O)$_5$]$_2$(EtO)Si(CH$_2$)$_3$SH,
[(C$_{12}$H$_{25}$O—(CH$_2$—CH$_2$O)$_6$]$_2$(EtO)Si(CH$_2$)$_3$SH,
[(C$_{13}$H$_{27}$O—(CH$_2$—CH$_2$O)$_2$]$_2$(EtO)Si(CH$_2$)$_3$SH,
[(C$_{13}$H$_{27}$O—(CH$_2$—CH$_2$O)$_3$]$_2$(EtO)Si(CH$_2$)$_3$SH,
[(C$_{13}$H$_{27}$O—(CH$_2$—CH$_2$O)$_4$]$_2$(EtO)Si(CH$_2$)$_3$SH,
[(C$_{13}$H$_{27}$O—(CH$_2$—CH$_2$O)$_5$]$_2$(EtO)Si(CH$_2$)$_3$SH,
[(C$_{13}$H$_{27}$O—(CH$_2$—CH$_2$O)$_6$]$_2$(EtO)Si(CH$_2$)$_3$SH,
[(C$_{14}$H$_{29}$O—(CH$_2$—CH$_2$O)$_2$]$_2$(EtO)Si(CH$_2$)$_3$SH,
[(C$_{14}$H$_{29}$O—(CH$_2$—CH$_2$O)$_3$]$_2$(EtO)Si(CH$_2$)$_3$SH,
[(C$_{14}$H$_{29}$O—(CH$_2$—CH$_2$O)$_4$]$_2$(EtO)Si(CH$_2$)$_3$SH,
[(C$_{14}$H$_{29}$O—(CH$_2$—CH$_2$O)$_5$]$_2$(EtO)Si(CH$_2$)$_3$SH,
[(C$_{14}$H$_{29}$O—(CH$_2$—CH$_2$O)$_6$]$_2$(EtO)Si(CH$_2$)$_3$SH,
[(C$_9$H$_{19}$O—(CH$_2$—CH$_2$O)$_2$]$_3$Si(CH$_2$)$_3$SH,
[(C$_9$H$_{19}$O—(CH$_2$—CH$_2$O)$_3$]$_3$Si(CH$_2$)$_3$SH,
[(C$_9$H$_{19}$O—(CH$_2$—CH$_2$O)$_4$]$_3$Si(CH$_2$)$_3$SH,
[(C$_9$H$_{19}$O—(CH$_2$—CH$_2$O)$_5$]$_3$Si(CH$_2$)$_3$SH,
[(C$_9$H$_{19}$O—(CH$_2$—CH$_2$O)$_6$]$_3$Si(CH$_2$)$_3$SH,
[(C$_{12}$H$_{25}$O—(CH$_2$—CH$_2$O)$_2$]$_3$Si(CH$_2$)$_3$SH,
[(C$_{12}$H$_{25}$O—(CH$_2$—CH$_2$O)$_3$]$_3$Si(CH$_2$)$_3$SH,
[(C$_{12}$H$_{25}$O—(CH$_2$—CH$_2$O)$_4$]$_3$Si(CH$_2$)$_3$SH,
[(C$_{12}$H$_{25}$O—(CH$_2$—CH$_2$O)$_5$]$_3$Si(CH$_2$)$_3$SH,
[(C$_{12}$H$_{25}$O—(CH$_2$—CH$_2$O)$_6$]$_3$Si(CH$_2$)$_3$SH,
[(C$_{13}$H$_{27}$O—(CH$_2$—CH$_2$O)$_2$]$_3$Si(CH$_2$)$_3$SH,
[(C$_{13}$H$_{27}$O—(CH$_2$—CH$_2$O)$_3$]$_3$Si(CH$_2$)$_3$SH,
[(C$_{13}$H$_{27}$O—(CH$_2$—CH$_2$O)$_4$]$_3$Si(CH$_2$)$_3$SH,
[(C$_{13}$H$_{27}$O—(CH$_2$—CH$_2$O)$_5$]$_3$Si(CH$_2$)$_3$SH,
[(C$_{13}$H$_{27}$O—(CH$_2$—CH$_2$O)$_6$]$_3$Si(CH$_2$)$_3$SH,
[(C$_{14}$H$_{29}$O—(CH$_2$—CH$_2$O)$_2$]$_3$Si(CH$_2$)$_3$SH,
[(C$_{14}$H$_{29}$O—(CH$_2$—CH$_2$O)$_3$]$_3$Si(CH$_2$)$_3$SH,
[(C$_{14}$H$_{29}$O—(CH$_2$—CH$_2$O)$_4$]$_3$Si(CH$_2$)$_3$SH,
[(C$_{14}$H$_{29}$O—(CH$_2$—CH$_2$O)$_5$]$_3$Si(CH$_2$)$_3$SH or
[(C$_{14}$H$_{29}$O—(CH$_2$—CH$_2$O)$_6$]$_3$Si(CH$_2$)$_3$SH.

Compounds of the general formula III $$((R''')_2 HalSi—R''-Hal \qquad III,$$

in which Hal, R and R'' have the abovementioned meaning and R''', independently of one another, are R or Hal, can be used as (haloorganyl)halosilanes for the preparation of organosilanes of the general formula I where X=SH.

(Chloroorganyl)chlorosilanes can preferably be used as (haloorganyl halosilanes).

For example,
3-chlorobutyl(trichlorosilane),
3-chloropropyl(trichlorosilane),
2-chloroethyl(trichlorosilane),
1-chloromethyl(trichlorosilane),
3-chlorobutyl(dichloromethoxysilane),
3-chloropropyl(dichloromethoxysilane),
2-chloroethyl(dichloromethoxysilane),
1-chloromethyl(dichloromethoxysilane),
3-chlorobutyl(dichloroethoxysilane),
3-chloropropyl(dichloroethoxysilane),
2-chloroethyl(dichloroethoxysilane),
1-chloromethyl(dichloroethoxysilane),
3-chlorobutyl(chlorodiethoxysilane),
3-chloropropyl(chlorodiethoxysilane),
2-chloroethyl(chlorodiethoxysilane),
1-chloromethyl(chlorodiethoxysilane),
3-chlorobutyl(chlorodimethoxysilane),
3-chloropropyl(chlorodimethoxysilane),
2-chloroethyl(chlorodimethoxysilane),
1-chloromethyl(chlorodimethoxysilane),
3-chlorobutyl(dichloromethylsilane),
3-chloropropyl(dichloromethylsilane),
2-chloroethyl(dichloromethylsilane),
1-chloromethyl(dichloromethylsilane),
3-chlorobutyl(chloro-)(methyl-)methoxysilane),
3-chloropropyl((chloro-)(methyl-)methoxysilane),
2-chloroethyl((chloro-)(methyl-)methoxysilane),
1-chloromethyl((chloro-)(methyl-)methoxysilane),
3-chlorobutyl((chloro-)(methyl-)ethoxysilane),
3-chloropropyl((chloro-)((methyl-)ethoxysilane),
2-chloroethyl((chloro-)(methyl-)ethoxysilane),
1-chloromethyl((chloro-)(methyl-)ethoxysilane),
3-chlorobutyl(chlorodimethylsilane),
3-chloropropyl(chlorodimethylsilane),
2-chloroethyl(chlorodimethylsilane) or
1-chloromethyl(chlorodimethylsilane) can be used as (haloorganyl)halosilanes.

The (haloorganyl)halosilane may be a (haloorganyl)halosilane of the general formula III or a mixture of (haloorganyl) chlorosilanes of the general formula III.

(Haloorganyl)alkoxysilane and (haloorganyl)chlorosilane can be used in the molar ratio of from 1:0.00001 to 1:0.8, preferably from 1:0.00001 to 1:0.5, particularly preferably from 1:0.00001 to 1:0.15, very particularly preferably from 1:0.00001 to 1:0.09.

Depending on the apparatus used and the desired effects, for example selectivity of the reaction, duration of the reaction, reactor throughput, reaction of (haloorganyl)alkyoxysilane and (haloorganyl)-chlorosilane with one another, reactor material and process sequence, the mixture of (haloorganyl) alkoxy-silane and (haloorganyl)chlorosilane can preferably be prepared before the addition of the alkali metal hydrogen sulphide.

The quality and type of the composition of the mixture of (haloorganyl)alkoxysilane and (haloorganyl)-chlorosilane can be assessed on the basis of the amount and type of the hydrolysable Si-halide bonds present in the mixture.

The amount of hydrolysable Si halide in the abovementioned mixtures of (haloorganyl)alkyloxysilane and (haloorganyl)chlorosilane, which can be determined by said analytical method, may be between 2 and 800 000 mg/kg, preferably between 10 and 80 000 mg/kg, particularly preferably between 10 and 40 000 mg/kg.

The amount of hydrolysable Si-halide in the abovementioned mixtures of (haloorganyl)alkoxysilane and (haloorganyl)chlorosilane, which can be determined by said analytical method, may be between 2 and 800 000 mg/kg, preferably between 500 and 800 000 mg/kg, particularly preferably between 5000 and 800 000 mg/kg, very particularly preferably between 50 000 and 800 000 mg/kg.

The amount of hydrolysable halide is determined by the following method: 80 ml of ethanol and 10 ml of acetic acid are added to not more than 20 g of sample in a 150 ml beaker. The halide content is titrated potentiographically with silver nitrate solution (c(AgNO$_3$)=0.01 mol/l).

The advantageous molar ratios of the mixtures of (haloorganyl)alkoxysilanes and (haloorganyl)halosilanes may be dependent, inter alia, on the number of Si-halogen functions of the (haloorganyl)halosilaness chosen.

For example, in the reaction of 3-chloropropyl-(trimethoxysilane) or 3-chloropropyl(triethoxysilane) and 3-chloropropyl(trichlorosilane), a molar ratio of from 1:0.00001 to 1:0.03 can preferably be used.

For example, in the reaction of 3-chloropropyl(methyldimethoxysilane) or 3-chloropropyl(methyldiethoxy-silane) and 3-chloropropyl(methyldichlorosilane), a molar ratio of from 1:0.00001 to 1:0.045 can preferably be used.

For example, in the reaction of 3-chloropropyl(di-methylmethoxysilane) or of 3-chloropropyl(dimethyl-ethoxysilane) and 3-chloropropyl(dimethylchlorosilane), a molar ratio of from 1:0.00001 to 1:0.09 can preferably be used.

The (haloorganyl)alkoxysilane and (haloorganyl)-halosilane can be mixed with one another in any desired sequence or manner, at any desired temperature and in any desired duration and only thereafter the alcohol and alkali metal hydrogen sulphide added together or in succession.

The (haloorganyl)halosilanes, alkali metal hydrogen sulphide and alcohol can be mixed with one another in any desired sequence or manner, at any desired temperature and in any desired duration and only thereafter the (haloorganyl)alkoxysilane added.

The (haloorganyl)alkoxysilane, alkali metal hydrogen sulphide and alcohol can be mixed with one another in any desired sequence or manner, at any desired temperature and in any desired duration and only thereafter the (haloorganyl)halosilane added.

The (haloorganyl)alkoxysilane, alcohol and additives can be mixed with one another in any desired sequence or manner, at any desired temperature and in any desired duration and only thereafter alkali metal hydrogen sulphide added.

Additives, alkali metal hydrogen sulphide and alcohol can be mixed with one another in any desired sequence or manner, at any desired temperature and in any desired duration and only thereafter the (haloorganyl)-alkoxysilane added.

The (haloorganyl)alkoxysilane, alkali metal hydrogen sulphide and alcohol can be mixed with one another in any desired sequence or manner, at any desired temperature and in any desired duration and only thereafter additives added.

The (haloorganyl)alkoxysilane, alkali metal hydrogen sulphide and additives can be mixed with one another in any desired sequence or manner, at any desired temperature and in any desired duration and only thereafter alcohol added.

Compounds of the general formula I where X=SH

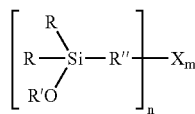

I can preferably be prepared by reacting water-containing alkali metal hydrogen sulphide with (haloorganyl)-alkoxysilanes of the general formula II

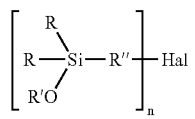

II in an alcohol in a closed vessel in the absence of air and under an elevated pressure in the presence of additives.

The reaction can preferably be carried out in the presence of $H_2S$.

The amount of added and/or liberated $H_2S$ in the preparation of compounds of the general formula I where X=SH may be less than 500 mol %, preferably less than 100 mol %, particularly preferably less than 50 mol %, very particularly preferably less than 15 mol % based on the amount of haloorganyl(alkoxysilane) used.

In the preparation of compounds of the general formula I where X=SH, the yield of crude product of the process according to the invention may be greater than 80%, preferably greater than 85%, particularly preferably greater than 90%, very particularly preferably greater than 95%, based on the theoretical yield with respect to the sum of (haloorganyl)alkoxysilane and (haloorganyl)halosilanes.

The yield of crude product may be the gravimetrically determined sum of all liquid compounds isolated after solvent and solids have been removed.

In the preparation of compounds of the general formula I where X=SH the amount of $R_2(R'O)Si-(R'')-S-(R'')-Si(OR')R_2$ formed as the by-product may be less than 15% by weight, preferably less than 10% by weight, particularly preferably less than 8% by weight, very particularly preferably less than 5% by weight, based on the amount of crude product.

In the preparation of compounds of the general formula I where X=SH, lithium hydrogen sulphide (LiSH), sodium hydrogen sulphide (NaSH), potassium hydrogen sulphide (KSH) and caesium hydrogen sulphide (CsSH) can, independently of one another, be used as water-containing sulphurization reagents.

The water-containing alkali metal hydrogen sulphides used in the preparation of compounds of the general formula I where X=SH can be added to the reaction as solids or in solution.

The alkali metal hydrogen sulphides required for the reaction in the preparation of compounds of the general formula I where X=SH can be formed before or during the reaction from sulphur-containing compounds, as described above.

The sulphur-containing compounds from which alkali metal hydrogen sulphides are formed before or during the reaction may be $H_2S$, alkali metal sulphides $Me_2S$ or alkali metal polysulphides $Me_2S_g$, preferably $Li_2S$, $Na_2S$, $K_2S$, $Na_2S_2$, $Na_2S_3$, $Na_2S_4$, $K_2S_2$, $K_{23}$ or $K_2S_4$.

In the preparation of compounds of the general formula I where X=SH, the sulphur-containing compounds from which alkali metal hydrogen sulphides are formed before or during the reaction can react completely or incompletely, reversibly or irreversibly by protonation to give alkali metal hydrogen sulphides.

In the preparation of compounds of the general formula I where X=SH, the protonation of the sulphur compounds from which alkali metal hydrogen sulphides are formed before or during the reaction can take place by means of $H_2S$ and/or organic and/or inorganic acids.

In the preparation of compounds of the general formula I where X=SH, the water-containing alkali metal hydrogen sulphides may contain more than 3% by weight, preferably more than 5% by weight, particularly preferably more than 10% by weight, very particularly preferably more than 12% by weight, exceedingly preferably more than 15% by weight, of water.

In the preparation of compounds of the general formula I where X=SH, the water-containing alkali metal hydrogen sulphides may contain more than 50% by weight, preferably more than 60% by weight, particularly preferably more than 65% by weight, very particularly preferably more than 70% by weight, of alkali metal hydrogen sulphide.

In the preparation of compounds of the general formula I where X=SH, the water-containing alkali metal hydrogen sulphides may contain, in addition to water, further secondary constituents in an amount of less than 50% by weight, preferably less than 30% by weight, particularly preferably less than 20% by weight, very particularly preferably less than 10% by weight.

In addition to water, further secondary constituents of water-containing alkali metal hydrogen sulphides may be, independently of one another, alkali metal carbonates, alkali metal bicarbonates, alkali metal hydroxides, alkali metal sulphides, alkali metal sulphates, alkali metal hydrogen sulphates, alkali metal thiosulphates and/or alkali metal hydrogen thiosulphates.

The further secondary constituents of water-containing alkali metal hydrogen sulphides may be inert or reactive towards the starting materials used and/or the products formed in the preparation of compounds of the general formula I where X=SH.

In the preparation of compounds of the general formula I where X=SH, the molar amount of alkali metal hydrogen sulphide used may exceed the sum of the molar amounts of the (haloorganyl)alkoxysilane used and of the (haloorganyl)halosilane used by from 1% to 50%, preferably by from 5 to 30%, particularly preferably by from 5 to 20%.

In the preparation of compounds of the general formula I where X=SH, amounts of alkali metal hydrogen sulphide smaller than the stoichiometrically required amounts may lead to an incomplete reaction. Consequently, either the product may be subsequently contaminated with starting material or a complicated purification is required in order to separate starting materials and products.

In the preparation of compounds of the general formula I where X=SH, the reaction temperature which is optimum in each case with regard to the yield of desired product and utilization of the reaction volume can vary an a function of the structure of the (haloorganyl)alkoxysilane used and of the alcohol used as solvent.

For example, in the preparation of compounds of the general formula I where X=SH, a reaction temperature between 40 and 95° C., preferably between 60 and 95° C., may be advantageous with respect to reaction times, amount of by-product and pressure build-up in reactions in methanol.

For example, in the preparation of compounds of the general formula I where X=SH, a reaction temperature between 50 and 130° C., preferably between 75 and 130° C., may be advantageous with respect to reaction times, amount of by-product and pressure build-up in reactions in ethanol.

In the preparation of compounds of the general formula I where X=SH, the closed container can preferably be a reaction vessel which is known from industry and which makes it possible to work at pressures up to 20 bar and temperatures up to 200° C. The closed container may have a heating/cooling circulation.

In the preparation of compounds of the general formula I where X=SH, the amount of by-product may be less than 20 mol %, preferably less than 15 mol %, particularly preferably less than 10 mol %, by the choice of the reaction conditions.

In addition to the mercaptoorganylsilane compounds desired for X=SH, the corresponding monosulphanes or disulphanes and, depending on the structure of the monomeric mercaptoorganylsilane compound, various combinations of dimeric or oligomeric siloxanes may form as by-products from products or from products with starting materials.

In a second preferred embodiment for the preparation of organosilanes of the general formula I where X=S and m=3.5-4.5, $Me_2S$ and sulphur can be used as the water-containing sulphurization reagent.

The reaction can be effected in the presence of a solvent or solvent mixture and of additives.

Water-containing sulphurization reagents which may be used are ammonium, alkali metal and alkaline earth metal sulphides and the polysulphides thereof or mixtures thereof. Ammonium-, lithium-, sodium-, potassium- and caesium-containing sulphurization reagents can preferably be used as the water-containing sulphurization reagents. Particularly preferably, $Na_2S$ hydrate or $K_2S$ hydrate can be used as the water-containing sulphurization reagents.

In the second embodiment, the $Me_2S$ may contain more than 10% by weight, preferably more than 15% by weight, particularly preferably more than 20% by weight, very particularly preferably more than 30% by weight, of water.

In the preparation of organosilanes of the general formula I where X=S and m=3.5-4.5, the water-containing sulphurization reagents may contain, in addition to water, further secondary constituents in an amount of less than 50% by weight, preferably less than 30% by weight, particularly preferably less than 20% by weight, very particularly preferably less than 10% by weight.

In the preparation of organosilanes of the general formula I where X=S and m=3.5-4.5, in addition to water, further secondary constituents of water-containing sulphurization reagents may be, independently of one another, alkali metal carbonates, alkali metal bicarbonates, alkali metal hydroxides, alkali metal sulphates, alkali metal hydrogen sulphates, alkali metal phosphates, alkali metal hydrogen phosphates, alkali metal dihydrogen phosphates, alkali metal thiosulphates and/or alkali metal hydrogen thiosulphates.

In the preparation of organosilanes of the general formula I where X=S and m=3.5-4.5, the molar amount of sulphurization reagent used can exceed the molar amount of the (haloorganyl)alkoxysilane used by from 0.1 mol % to 50 mol %, preferably by from 0.1 to 30 mol %, particularly preferably by from 0.1 to 5 mol %.

In the preparation of organosilanes of the general formula I where X=S and m=3.5-4.5, amounts of sulphurization reagent which are smaller than the stoichiometrically required amounts can lead to an incomplete conversion. Consequently, either the product is subsequently contaminated with starting material or complicated working-up is necessary in order to separate starting materials and products from another.

The sulphur may be added in the form of sulphur powder or sulphur granules or in liquid form.

In the second embodiment, the solvent or solvent mixture can preferably be an organic solvent or solvent mixture comprising organic solvents. Solvents or solvent mixtures may be, for example, alcohols or water-containing alcohols. The water content of the solvent or solvent mixture may be from 0.1 to 50% by weight, preferably from 0.1 to 25% by weight, particularly preferably from 0.1 to 10% by weight, very particularly preferably from 0.1 to 5% by weight.

In the preparation of organosilanes of the general formula I where X=S and m=3.5-4.5, the amount of alcohol may be at least 5% by volume, preferably from 10 to 300% by volume, particularly preferably from 10 to 100% by volume, very particularly preferably from 10 to 25% by volume, of the silane component or silane components used.

In the preparation of organosilanes of the general formula I where X=S and m=3.5-4.5, additives can, independently of one another, be added to the reaction mixture before, during and at the end of the reaction. The additives are preferably added before the reaction.

Additives may be (alkali metal ion)$H_2PO_4$, (alkali metal ion)$_2HPO_4$, (alkali metal ion)$_3PO_4$, (alkali metal ion)$HCO_3$, (alkali metal ion)$_2CO_3$, (alkali metal ion)$_2SO_1$ or (alkali metal ion)$HSO_4$. The corresponding alkaline earth metal salts can also be used as additives.

The reaction for the preparation of organosilanes of the general formula I where X=S and m=3.5-4.5 can preferably be carried out in the absence of air.

In the second embodiment, the organosilanes of the general formula I may be mixtures of organosilanes of the general formula I having an average sulphur chain length of m=3.5-4.5, it being possible for the organosilanes to have sulphur chains of S1 to S12, for example in the case of [(MeO)$_3$Si(CH$_2$)$_3$]$_2$S$_m$:
[(MeO)$_3$Si(CH$_2$)$_3$]$_2$S, [(MeO)$_3$Si(CH$_2$)$_3$]$_2$S$_2$,
[(MeO)$_3$Si(CH$_2$)$_3$]$_2$S$_3$, [(MeO)$_3$Si(CH$_2$)$_3$]$_2$S$_4$,
[(MeO)$_3$Si(CH$_2$)$_3$]$_2$S$_5$, [(MeO)$_3$Si(CH$_2$)$_3$]$_2$S$_6$,
[(MeO)$_3$Si(CH$_2$)$_3$]$_2$S$_7$, [(MeO)$_3$Si(CH$_2$)$_3$]$_2$S$_8$,
[(MeO)$_3$Si(CH$_2$)$_3$]$_2$S$_9$, [(MeO)$_3$Si(CH$_2$)$_3$]$_2$S$_{10}$,
[(MeO)$_3$Si(CH$_2$)$_3$]$_2$S$_{11}$, [(MeO)$_3$Si(CH$_2$)$_3$]$_2$S$_{12}$,
[(MeO)$_3$Si(CH$_2$)$_3$]$_2$S, in the case of [E(EtO)$_3$Si(CH$_2$)$_3$]$_2$S$_m$:
[(EtO)$_3$Si(CH$_2$)$_3$]$_2$S$_2$, [(EtO)$_3$Si(CH$_2$)$_3$]$_2$S$_3$,
[(EtO)$_3$Si(CH$_2$)$_3$]$_2$S$_4$, [(EtO)$_3$Si(CH$_2$)$_3$]$_2$S$_5$,
[(EtO)$_3$Si(CH$_2$)$_3$]$_2$S$_6$, [(EtO)$_3$Si(CH$_2$)$_3$]$_2$S$_7$,
[(EtO)$_3$Si(CH$_2$)$_3$]$_2$S$_8$, [(EtO)$_3$Si(CH$_2$)$_3$]$_2$S$_9$,
[(EtO)$_3$Si(CH$_2$)$_3$]$_2$S$_{10}$, [(EtO)$_3$Si(CH$_2$)$_3$]$_2$S$_{11}$,
[(EtO)$_3$Si(CH$_2$)$_3$]$_2$S$_{12}$, in the case of [(C$_3$H$_7$O)$_3$Si(CH$_2$)$_3$]$_2$S$_m$:
[(C$_3$H$_7$O)$_3$Si(CH$_2$)$_3$]$_2$S, [(C$_3$H$_7$O)$_3$Si(CH$_2$)$_3$]$_2$S$_2$,
[(C$_3$H$_7$O)$_{3i(CH2)}$$_3$]$_2$S$_3$, [(C$_3$H$_7$O)$_3$Si(CH$_2$)$_3$]$_2$S$_4$,
[(C$_3$H$_7$O)$_3$Si(CH$_2$)$_3$]$_2$S$_5$, [(C$_3$H$_7$O)$_3$Si(CH$_2$)$_3$]$_2$S$_6$,
[(C$_3$H$_7$O)$_3$Si(CH$_2$)$_3$]$_2$S$_7$, [(C$_3$H$_7$O)$_3$Si(CH$_2$)$_3$]$_2$S$_8$,
[(C$_3$H$_7$O)$_3$Si(CH$_2$)$_3$]$_2$S$_9$, [(C$_3$H$_7$O)$_{3i(CH2)}$$_3$]$_2$S$_{10}$,
[(C$_3$H$_7$O)$_3$Si(CH$_2$)$_3$]$_2$S$_{11}$, [(C$_3$H$_7$O)$_3$Si(CH$_2$)$_3$]$_2$S$_{12}$.

Organosilanes of the general formula I may be:
[(MeO)$_3$Si(CH$_2$)$_3$]$_2$S$_m$, [(EtO)$_3$Si(CH$_2$)$_3$]$_2$S$_m$,
[(C$_3$H$_7$O)$_3$Si(CH$_2$)$_3$]$_2$S$_m$,
[(C$_{12}$H$_{25}$O)$_3$Si(CH$_2$)$_3$]S$_m$, [(CH$_2$)$_3$Si(C$_{12}$H$_{25}$O)$_3$],
[(C$_{14}$H$_{29}$O)$_3$Si(CH$_2$)$_3$]S$_m$, [(CH$_2$)$_3$Si(C$_{14}$H$_{29}$O)$_3$],
[(C$_{16}$H$_{33}$O)$_3$Si(CH$_2$)$_3$]S$_m$, [(CH$_2$)$_3$Si(C$_{16}$H$_{33}$O)$_3$],
[(C$_{18}$H$_{37}$O)$_3$Si(CH$_2$)$_3$]S$_m$[(CH$_2$)$_3$Si(C$_{19}$H$_{37}$O)$_3$],
[(C$_{12}$H$_{25}$O)$_3$Si(CH$_2$)$_3$]S$_m$[(CH$_2$)$_3$Si(C$_{12}$H$_{25}$O)$_3$],
[(C$_{14}$H$_{29}$O)$_3$Si(CH$_2$)$_3$]S$_m$[(CH$_2$)$_3$Si(C$_{14}$H$_{29}$O)$_3$],
[(C$_{16}$H$_{33}$O)$_3$Si(CH$_2$)$_3$]S$_m$[(CH$_2$)$_3$Si(C$_{16}$H$_{33}$O)$_3$],
[(C$_{18}$H$_{37}$O)$_3$Si(CH$_2$)$_3$]S$_m$[(CH$_2$)$_3$Si(C$_{18}$H$_{37}$O)$_3$],
[(C$_{12}$H$_{25}$O)$_2$(CH$_3$)Si(CH$_2$)$_3$]S$_m$[(CH$_2$)$_3$Si(CH$_3$)(C$_{12}$H$_{25}$O)$_2$],
[(C$_{12}$H$_{25}$O)(C$_{14}$H$_{29}$O)(CH$_3$)Si(CH$_2$)$_3$]S$_m$[(CH$_2$)$_3$Si(CH$_3$)(C$_{12}$H$_{25}$O)(C$_{14}$—H$_{25}$O)],
[(C$_{12}$H$_{25}$O)(C$_{14}$H$_{21}$O)(CH$_3$)Si(CH$_2$)$_3$]S$_m$[(CH$_2$)$_3$Si(CH$_3$)(C$_{12}$H$_{25}$O)(C$_{12}$—H$_{25}$O)],
[(C$_{12}$H$_{25}$O)(C$_{16}$H$_{33}$O)(CH$_3$)Si(CH$_2$)$_3$]S$_m$[(CH$_2$)$_3$Si(CH$_3$)(C$_{12}$H$_{25}$O)(C$_{16}$—H$_{33}$O)],
[(C$_{12}$H$_{25}$O)(C$_{18}$H$_{37}$O)(CH$_3$)Si(CH$_2$)$_3$]S$_m$[(CH$_2$)$_3$Si(CH$_3$)(C$_{12}$H$_{25}$O)—(C$_{12}$H$_{25}$O)(C$_{18}$H$_{37}$O)],
[(C$_{12}$H$_{25}$O)(C$_{18}$H$_{37}$O)(CH$_3$)Si(CH$_2$)$_3$]S$_m$[(CH$_2$)$_3$Si(CH$_3$)(C$_{14}$H$_{25}$O)—(C$_{18}$H$_{37}$O)],
[(C$_{14}$H$_{29}$O)$_2$(CH$_3$)Si(CH$_2$)$_3$]S$_m$[(CH$_2$)$_3$Si(CH$_3$)(C$_{14}$H$_{29}$O)$_2$],
[(C$_{14}$H$_{29}$O)(C$_{16}$H$_{33}$O)(CH$_3$)Si(CH$_2$)$_3$]S$_m$[(CH$_2$)$_3$Si(CH$_3$)(C$_{14}$H$_{33}$O)—(C$_{16}$H$_{33}$O)],
[(C$_{14}$H$_{29}$O)(C$_{18}$H$_{37}$O)(CH$_3$)Si(CH$_2$)$_3$]S$_m$[(CH$_2$)$_3$Si(CH$_3$)(C$_{14}$H$_{29}$O)—(C$_{18}$H$_{37}$O)],
[(C$_{16}$H$_{33}$O)$_2$(CH$_3$)Si(CH$_2$)$_3$]S$_m$[(CH$_2$)$_3$Si(CH$_3$)(C$_{16}$H$_{33}$O)$_2$],
[(C$_{16}$H$_{33}$O)(C$_{18}$H$_{37}$O)(CH$_3$)Si(CH$_2$)$_3$]S$_m$[(CH$_2$)$_3$Si(CH$_3$)(C$_{16}$H$_{33}$O)—(C$_{18}$H$_{37}$O)],
[(C$_{18}$H$_{37}$O)$_2$(CH$_3$)Si(CH$_2$)$_3$]S$_m$[(CH$_2$)$_3$Si(CH$_3$)(C$_{18}$H$_{37}$O)$_2$],
[(C$_{12}$H$_{25}$O)(CH$_3$)$_2$Si(CH$_2$)$_3$]S$_m$[(CH$_2$)$_3$Si(CH$_3$)$_2$(C$_{12}$H$_{25}$O)],
[(C$_{12}$H$_{25}$O)(CH$_3$)$_2$Si(CH$_2$)$_3$]S$_m$[(CH$_2$)$_3$Si(CH$_3$)$_2$(C$_{14}$H$_{29}$O)],
[(C$_{12}$H$_{25}$O)(CH$_3$)$_2$Si(CH$_2$)$_3$]S$_m$[(CH$_2$)$_3$Si(CH$_3$)$_2$(C$_{16}$H$_{33}$O)],
[(C$_{12}$H$_{25}$O)(CH$_3$)$_2$Si(CH$_2$)$_3$]S$_m$[(CH$_2$)$_3$Si(CH$_3$)$_2$(C$_{18}$H$_{37}$O)],
[(C$_{14}$H$_{29}$O)(CH$_3$)$_2$Si(CH$_2$)$_3$]S$_m$[(CH$_2$)$_3$Si(CH$_3$)$_2$(C$_{14}$H$_{29}$O)],
[(C$_{14}$H$_{29}$O)(CH$_3$)$_2$Si(CH$_2$)$_3$]S$_m$[(CH$_2$)$_3$Si(CH$_3$)$_2$(C$_{16}$H$_{33}$O)],
[(C$_{14}$H$_{29}$O)(CH$_3$)$_2$Si(CH$_2$)$_3$]S$_m$[(CH$_2$)$_3$Si(CH$_3$)$_2$(C$_{18}$H$_{37}$O)],
[(C$_{16}$H$_{33}$O)(CH$_3$)$_2$Si(CH$_2$)$_3$]S$_m$[(CH$_2$)$_3$Si(CH$_3$)$_2$(C$_{16}$H$_{33}$O)],
[(C$_{16}$H$_{33}$O)(CH$_3$)$_2$Si(CH$_2$)$_3$]S$_m$[(CH$_2$)$_3$Si(CH$_3$)$_2$(C$_{18}$H$_{37}$O)] and
[(C$_{18}$H$_{37}$O)(CH$_3$)$_2$Si(CH$_2$)$_3$]S$_m$[(CH$_2$)$_3$Si(CH$_3$)$_2$(C$_{18}$H$_{37}$O)] where m=3.5-4.5.

Compounds of the general formula I where X=S and m=3.5-4.5

$$\left[\begin{array}{c} R \\ R-Si-R'' \\ R'O \end{array}\right]_n -X_m \qquad I$$

can preferably be prepared by reacting water-containing sulphurization reagents with (haloorganyl)alkoxysilanes of the general formula II $$\left[\begin{array}{c} R \\ R-Si-R'' \\ R'O \end{array}\right]-Hal \qquad II$$

in an organic solvent or solvent mixture which may contain water, for example alcohol, in an open or closed vessel, optionally under pressure and in the absence of air. Very particularly preferably, the reaction of water-containing sulphurization reagents with (haloorganyl)alkoxysilanes of the general formula II $$\left[\begin{array}{c} R \\ R-Si-R'' \\ R'O \end{array}\right]-Hal \qquad II$$

can be carried out in an open vessel in the absence of air at the pressure generated under these conditions.

The reaction temperature which is optimum in each case with regard to the yield of desired product may vary depending on the structure of the (haloorganyl)alkoxy-silane used and of the alcohol used as solvent, with regard to type and amount.

The reaction temperature may be between the ambient temperature and the boiling point of the solvent or solvent mixture used. The reaction temperature is preferably between 20° C. and the boiling point of the solvent or solvent mixture used; the reaction temperature is particularly preferably between 40° C. and 80° C., very particularly preferably between 60° C. and 70° C.

In the preparation of organosilanes of the general formula I where X=S and m=3.5-4.5, the yield of the product of the process according to the invention may be greater than 80%, preferably greater than 85%, particularly preferably greater than 90%, very particularly preferably greater than 98%, based on the theoretical yield with respect to the (haloorganyl)alkoxysilane.

In the preparation of organosilanes of the general formula I where X=S and m=3.5-4.5, the yield of crude product may be the gravimetrically determined sum of all liquid compounds isolated, after solvents or solvent mixtures and solids have been removed.

In the preparation of organosilanes of the general formula I where X=S and m=3.5-4.5, the composition of compounds or mixtures of compounds of the general formula I where X=S and m=3.5-4.5 can be influenced in an active and targeted manner by the choice of the composition of the mixtures of (haloorganyl)alkoxy-silanes, sulphurization reagents and alcohol used, amount of alcohol and additives.

The mixture of appropriate (haloorganyl)alkoxysilane and additives used in the preparation of organosilanes of the general formula I where X=S and m=3.5-4.5 can be prepared before the addition of the sulphurization reagents, depending on the apparatus used and the desired effects which in some cases can be influenced independently of one another, for example selectivity of the reaction, duration of the reaction, reactor throughput, reaction of (haloorganyl)alkoxysilane and sulphurization reagent with one another, value m in X=$S_m$, reaction of alkali metal sulphide and sulphur, the reaction material or the process sequence.

The mixture of appropriate sulphurization reagents, sulphur and additives used in the preparation of organosilanes of the general formula I where X=S and m=3.5-4.5 can be prepared before the addition of the (haloorganyl) alkoxysilane, depending on the apparatus used and the desired effects which in some cases can be influenced independently of one another, the reactor material or the process sequence.

The quality of the (haloorganyl)alkoxysilanes used in the preparation of organosilanes of the general formula I where X=S and m=3.5-4.5 can be assessed on the basis of the amount of hydrolysable Si-halide bonds.

In the preparation of organosilanes of the general formula I where X=S and m=3.5-4.5, the amount of hydrolysable Si-halide in the (haloorganyl)alkoxysilane of the formula II, which can be determined by said analytical method, may be between 2 and 10 000 mg/kg, preferably between 10 and 1000 mg/kg, particularly preferably between 10 and 100 mg/kg, very particularly preferably between 10 and 50 mg/kg.

The amount of hydrolzable halide in the mixtures comprising haloorganyl(alkoxysilane) and additives used in the preparation of organosilanes of the general formula I where X=S and m=1.5-4.5 is determined by the following method: 80 ml of ethanol and 10 ml of acetic acid are added to not more than 20 g of the sample in a 150 ml beaker. The halide content is titrated potentiographically with silver nitrate solution ($c(AgNO_3)$=0.01 mol/l).

In the preparation of organosilanes of the general formula I where X=S and m=3.5-4.5, the (haloorganyl)alkoxysilane and the additives can be mixed with one another in any desired sequence or manner, at any desired temperature and in any desired duration and only thereafter the alcohol and sulphurization reagents added together or in succession.

In the preparation of organosilanes of the general formula I where X=S and m=3.5-4.5, additives, sulphurization reagents and alcohol can be mixed with one another in any desired sequence or manner, at any desired temperature and in any desired duration and only thereafter the (haloorganyl)alkoxysilane added. In the preparation of organosilanes of the general formula I where X=S and m=3.5-4.5, the (haloorganyl)-alkoxysilane, sulphurization reagents and alcohol can be mixed with one another in any desired sequence or manner, at any desired temperature and in any desired duration and only thereafter additives added.

In the preparation of organosilanes of the general formula I where X=S and m=3.5-4.5, the (haloorganyl)-alkoxysilane, sulphurization reagents and additives can be mixed with one another in any desired sequence or manner, at any desired temperature and in any desired duration and only thereafter alcohol added.

In the preparation of organosilanes of the general formula I where X=S and m=3.5-4.5, sulphurization reagents and additives can be mixed with one another in any desired sequence or manner, at any desired temperature and in any desired duration and only thereafter the alcohol and (haloorganyl)alkoxysilane added together or in succession.

The water-containing sulphurization reagents, of which $Na_2S$ hydrate and $K_2S$ hydrate are particularly preferably used, can be metered to the reaction mixture before and/or during the reaction.

The water-containing sulphurization reagents used in the preparation of organosilanes of the general formula I where X=S and m=3.5-4.5 can be added to the reaction as solids or in solution.

The water-containing sulphurization reagents required for the reaction in the preparation of organosilanes of the general formula I where X=S and m=3.5-4.5 may be formed before or during the reaction from sulphur-containing compounds.

The sulphur-containing compounds from which sulphurization reagents are formed before or during the reaction in the preparation of organosilanes of the general formula I where X=S and m=3.5-4.5 may be sulphur, alkali metal sulphides $Me_2S$ or alkali metal polysulphides $Me_2S_g$, preferably $Na_2S$, $K_2S$, $Na_2S_2$, $Na_2S_3$, $Na_2S_4$, $K_2S_2$, $K_2S_3$ or $K_2S_4$.

In the preparation of organosilantes of the general formula I where X=S and m=3.5-4.5, raw materials which contain more than 30% by weight, preferably more than 40% by weight, particularly preferably more than 50% by weight, very particularly preferably more than 59% by weight of $Me_2S$, or which contain more than 20% by weight, preferably more than 30% by weight, particularly preferably more than 40% by weight, very particularly preferably more than 50% by weight, $Me_2S_g$, can be used, independently of one another, for the preparation of the reaction products of $Me_2S$, or $Me_2S_g$ and sulphur.

For the preparation of organosilanes of the general formula I where X=S and m=3.5-4.5, the reaction container can preferably be a reaction vessel which is known from industry and makes it possible to work at pressures of from 0 to 10 bar and temperatures up to 200° C. The reaction container may have a heating/cooling circulation.

In the preparation of organosilanes of the general formula I where X=S and m=3.5-4.5, the amount of by-products can, through the choice of the reaction conditions, be less than 10 mol %, preferably less than 5 mol %, particularly preferably less than 2 mol %.

In the preparation of organosilanes of the general formula I where X=S and m=3.5-4.5, the amount of residual haloorganyl(alkoxysilane) starting material can, through the choice of the reaction conditions, be less than 10% by weight, preferably less than 5% by weight, particularly preferably less than 2% by weight, very particularly preferably less than 1.5% by weight.

In the second embodiment, the solvent/water mixture can be removed from the crude product suspension, preferably at reduced pressure, and the resulting suspension, containing the organosilane of the general formula I which has formed, can be separated from the solid, preferably by centrifuging, decanting or filtration.

The solvent/water mixture can be removed at a pressure of from 800 mbar to 10 mbar, preferably by distillation. The solvent/water mixture may contain ethanol.

The resulting suspension may contain Me(Hal), for example NaCl, buffer salts and organosilanes of the general formula I.

The solvent can be removed from the crude product suspension, the mixture containing the organosilanes of the general formula (I) and the solid Me(Hal) can be mixed with water, containing at least one buffer, and the phases forming can be separated.

The working-up of the crude product suspension can include a filtration and removal of solid constituents. The working-up of the crude product suspension can include a distillation and removal of volatile constituents. The working-up of the crude product suspension can include first a distillation and then a filtration. The working-up of the crude product suspension can include first a filtration and then a distillation. The working-up of the crude product suspension can include first a filtration, then a distillation and thereafter a further filtration.

The salt-containing crude product suspension present after the reaction can be worked up at atmospheric pressure or reduced pressure, preferably at a reduced pressure between 1 and 700 mbar, particularly preferably between 5 and 500 mbar, very particularly preferably between 10 and 250 mbar.

The salt-containing product suspension present after the reaction can be worked up at ambient temperature or elevated temperature, preferably between 20 and 200° C., particularly preferably between 40 and 150° C., very particularly preferably between 50 and 100° C.

During the working-up, a mixture of product and solid may form. During the working-up, a mixture of product and alcohol may form. During the working-up, a mixture of product, alcohol and water may form. During the working-up, a mixture of product and water may form. During the working-up, a mixture of product, solid and water may form. During the working-up, a mixture of product, Me(Hal), for example sodium chloride, and water may form. During the working-up, a mixture of product, Me(Hal), for example sodium chloride, alcohol and water may form.

Water may be added to a mixture of product and/or solid and/or alcohol and/or water.

The water can be added in an amount of from 1 to 200% by weight, preferably from 1 to 100% by weight, particularly preferably from 5 to 75% by weight, very particularly preferably from 5 to 50% by weight, based on the product.

The water may be demineralized water. The water may contain a buffer, for example sodium bicarbonate or sodium carbonate. The buffer content of the water may be 1% by weight-20% by weight, preferably 2% by weight-5% by weight.

The added water may have a pH of between 3 and 11, preferably between 4 and 10, particularly preferably between 5 and 9, very particularly preferably between 7 and 9.

The pH of the added water may be adjusted by the buffer, for example $NaHCO_3$.

The solid can preferably be present in the aqueous phase. The salt Me(Hal), for example sodium chloride, can preferably be present in the aqueous phase.

The product may separate from the salt-containing aqueous phase by phase separation. After the phase separation, the product can be separated from the salt-containing aqueous phase. After separation from the salt-containing phase, the product can be dried.

In a third preferred embodiment for the preparation of organosilanes of the general formula I where X=S and m=1.5-4.5, preferably m=1.8-2.5 or m=3.4-4.0, particularly preferably m=2.0-2.3 or m=3.6-3.85, very particularly preferably m=2.05-2.2 or m=3.65-3.8, alkali metal hydrogen sulphides $Me_2S$, $Me_2SO$ and any desired combinations thereof and optionally additionally sulphur and/or $H_2S$ can be used as water-containing sulphurization reagents and the reaction can be carried out in a closed vessel in the absence of air.

In the preparation of organosilanes of the general formula I where X=S and m=1.5-4.5, additives can, independently of one another, be added to the reaction mixture before, during and at the end of the reaction.

Additives may be $H_2S$, (alkali metal ion)$H_2PO_4$, (alkali metal ion)$_2HPO_4$, (alkali metal ion)$_3PO_4$, (alkali metal ion)$HCO_3$, (alkali metal ion)$_2CO_3$, (alkali metal ion)$_2SO_4$ or (alkali metal ion)$HSO_4$.

In the preparation of organosilanes of the general formula I where X=S and m=1.5-4.5, the reaction can preferably be carried out in a closed vessel.

In the preparation of organosilanes of the general formula I where X=S and m=1.5-4.5, the reaction can be carried out under elevated pressure of from >0.1 bar to <20 bar, preferably from >0.1 bar to <15 bar, particularly preferably from >0.5 bar to <10 bar, very particularly preferably from >0.5 bar to <6 bar.

In the preparation of organosilanes of the general formula I where X=S and m=1.5-4.5, the reaction can preferably be carried out in the absence of air.

In the preparation of organosilanes of the general formula I where X=S and m=1.5-4.5, the reaction can preferably be carried out in such a way that the gas forming cannot escape from the reaction space.

In the preparation of organosilanes of the general formula I where X=S and m=1.5-4.5, the amount of alcohol may be at least 5% by volume, preferably from 10 to 300% by volume, particularly preferably from 10 to 200% by volume, very particularly preferably from 10 to 150% by volume, of the silane components used. The ethanol used may contain water.

In the third embodiment, the organosilanes of the general formula x may be mixtures of organosilanes of the general formula I having an average sulphur chain length of m=1.5-4.5, it being possible for the organosilanes to have sulphur chains from S1 to S12, for example in the case of $[(MeO)_3Si(CH_2)_3]_2S_m$:
$[(MeO)_3Si(CH_2)_3]_2S$, $[(MeO)_3Si(CH_2)_3]_2S_2$,
$[(MeO)_3Si(CH_2)_3]_2S_3$, $[(MeO)_3Si(CH_2)_3]_2S_4$,
$[(MeO)_3Si(CH_2)_3]_2S_5$, $[(MeO)_3Si(CH_2)_3]_2S_6$,

[(MeO)$_3$Si(CH$_2$)$_3$]$_2$S$_7$, [(MeO)$_3$Si(CH$_2$)$_3$]$_2$S$_8$,
[(MeO)$_3$Si(CH$_2$)$_3$]$_2$S$_9$, [(MeO)$_3$Si(CH$_2$)$_3$]$_2$S$_{10}$,
[(MeO)$_3$Si(CH$_2$)$_3$]$_2$S$_{11}$, [(MeO)$_3$Si(CH$_2$)$_3$]$_2$S$_{12}$, in the case of [(EtO)$_3$Si(CH$_2$)$_3$]$_2$S$_m$:
[(EtO)$_3$Si(CH$_2$)$_3$]$_2$S, [(EtO)$_3$Si(CH$_2$)$_3$]$_2$S$_2$,
[(EtO)$_3$Si(CH$_2$)$_3$]$_2$S$_3$, [(EtO)$_3$Si(CH$_2$)$_3$]$_2$S$_4$,
[(EtO)$_3$Si(CH$_2$)$_3$]$_2$S$_5$, [(EtO)$_3$Si(CH$_2$)$_3$]$_2$S$_6$,
[(EtO)$_3$Si(CH$_2$)$_3$]$_2$S$_7$, [(EtO)$_3$Si(CH$_2$)$_3$]$_2$S$_8$,
[(EtO)$_3$Si(CH$_2$)$_3$]$_2$S$_9$, [(EtO)$_3$Si(CH$_2$)$_3$]$_2$S$_{10}$,
[(EtO)$_3$Si(CH$_2$)$_3$]$_2$S$_{10}$, [(EtO)$_3$Si(CH$_2$)$_3$]$_2$S$_{12}$, in the case of [(C$_3$H$_7$O)$_3$Si(CH$_2$)$_3$]$_2$S$_m$:
[(C$_3$H$_7$O)$_3$Si(CH$_2$)$_3$]$_2$S, [(C$_3$H$_7$O)$_3$Si(CH$_2$)$_3$]$_2$S$_2$,
[(C$_3$H$_7$O)$_3$Si(CH$_2$)$_3$]$_2$S$_3$, [(C$_3$H$_7$O)$_3$Si(CH$_2$)$_3$]$_2$S$_4$,
[(C$_3$H$_7$O)$_3$Si(CH$_2$)$_3$]$_2$S$_5$, [(C$_3$H$_7$O)$_3$Si(CH$_2$)$_3$]$_2$S$_6$,
[(C$_3$H$_7$O)$_3$Si(CH$_2$)$_3$]$_2$S$_7$, [(C$_3$H$_7$O)$_3$Si(CH$_2$)$_3$]$_2$S$_8$,
[(C$_3$H$_7$O)$_3$Si(CH$_2$)$_3$]$_2$S$_9$, [(C$_3$H$_7$O)$_3$Si(CH$_2$)$_3$]$_2$S$_{10}$,
[(C$_3$H$_7$O)$_3$Si(CH$_2$)$_3$]$_2$S$_{11}$, [(C$_3$H$_7$O)$_3$Si(CH$_2$)$_3$]$_2$S$_{12}$.

Organosilanes of the general formula I may be:
[(MeO)$_3$Si(CH$_2$)$_3$]$_2$S$_m$, [(EtO)$_3$Si(CH$_2$)$_3$]$_2$S$_m$,
[(C$_3$H$_7$O)$_3$Si(CH$_2$)$_3$]$_2$S$_m$,
[(C$_{12}$H$_{25}$O)$_3$Si(CH$_2$)$_3$]S$_m$[(CH$_2$)$_3$Si(C$_{12}$H$_{25}$O)$_3$],
[(C$_{14}$H$_{29}$O)$_3$Si(CH$_2$)$_3$]S$_m$[(CH$_2$)$_3$Si(C$_{14}$H$_{29}$O)$_3$],
[(C$_{16}$H$_{33}$O)$_3$Si(CH$_2$)$_3$]S$_m$[(CH$_2$)$_3$Si(C$_{16}$H$_{33}$O)$_3$],
[(C$_{18}$H$_{37}$O)$_3$Si(CH$_2$)$_3$]S$_m$[(CH$_2$)$_3$Si(C$_{18}$H$_{37}$O)$_3$],
[(C$_{12}$H$_{25}$O)$_3$Si(CH$_2$)$_3$]S$_m$[(CH$_2$)$_3$Si(C$_{14}$H$_{29}$O)$_3$],
[(C$_{14}$H$_{29}$O)$_3$Si(CH$_2$)$_3$]S$_m$[(CH$_2$)$_3$Si(C$_{16}$H$_{33}$O)$_3$],
[(C$_{16}$H$_{33}$O)$_3$Si(CH$_2$)$_3$]S$_m$[(CH$_2$)$_3$Si(C$_{18}$H$_{37}$O)$_3$],
[(C$_{18}$H$_{37}$O)$_3$Si(CH$_2$)$_3$]S$_m$[(CH$_2$)$_3$Si(C$_{14}$H$_{29}$O)$_3$],
[(C$_{12}$H$_{25}$O)$_2$(CH$_3$)Si(CH$_2$)$_3$]S$_m$[(CH$_2$)$_3$Si(CH$_3$)(C$_{12}$H$_{25}$O)$_2$],
[(C$_{12}$H$_{25}$O)(C$_{14}$H$_{29}$O)(CH$_3$)Si(CH$_2$)$_3$]S$_m$[(CH$_2$)$_3$Si(CH$_3$)(C$_{12}$H$_{25}$O)(C$_{14}$H$_{25}$O)],
[(C$_{12}$H$_{25}$O)(C$_{14}$H$_{29}$O)(CH$_3$)Si(CH$_2$)$_3$]S$_m$[(CH$_2$)$_3$Si(CH$_3$)(C$_{12}$H$_{25}$O)(C$_{12}$H$_{25}$O)],
[(C$_{12}$H$_{25}$O)(C$_{16}$H$_{33}$O)(CH$_3$)Si(CH$_2$)$_3$]S$_m$[(CH$_2$)$_3$Si(CH$_3$)(C$_{12}$H$_{25}$O)(C$_{16}$H$_{33}$O)],
[(C$_{12}$H$_{25}$O)(C$_{18}$H$_{37}$O)(CH$_3$)Si(CH$_2$)$_3$]S$_m$[(CH$_2$)$_3$Si(CH$_3$)(C$_{12}$H$_{25}$O)(C$_{18}$H$_{37}$O)],
[(C$_{12}$H$_{25}$O)(C$_{18}$H$_{37}$O)(CH$_3$)Si(CH$_2$)$_3$]S$_m$[(CH$_2$)$_3$Si(CH$_3$)(C$_{18}$H$_{37}$O)$_2$],
[(C$_{14}$H$_{29}$O)$_2$(CH$_3$)Si(CH$_2$)$_3$]S$_m$[(CH$_2$)$_3$Si(CH$_3$)(C$_{14}$H$_{29}$O)$_2$],
[(C$_{14}$H$_{29}$O)(C$_{16}$H$_{33}$O)(CH$_3$)Si(CH$_2$)$_3$]S$_m$[(CH$_2$)$_3$Si(CH$_3$)(C$_{14}$H$_{29}$O)(C$_{16}$H$_{33}$O)],
[(C$_{14}$H$_{29}$O)(C$_{18}$H$_{37}$O)(CH$_3$)Si(CH$_2$)$_3$]S$_m$[(CH$_2$)$_3$Si(CH$_3$)(C$_{14}$H$_{29}$O)(C$_{18}$H$_{37}$O)],
[(C$_{16}$H$_{33}$O)$_2$(CH$_3$)Si(CH$_2$)$_3$]S$_m$[(CH$_2$)$_3$Si(CH$_3$)(C$_{16}$H$_{33}$O)$_2$],
[(C$_{16}$H$_{33}$O)(C$_{18}$H$_{37}$O)(CH$_3$)Si(CH$_2$)$_3$]S$_m$[(CH$_2$)$_3$Si(CH$_3$)(C$_{16}$H$_{33}$O)(C$_{18}$H$_{37}$O)],
[(C$_{18}$H$_{37}$O)$_2$(CH$_3$)Si(CH$_2$)$_3$]S$_m$[(CH$_2$)$_3$Si(CH$_3$)(C$_{18}$CH$_{37}$O)$_2$],
[(C$_{12}$H$_{25}$O)(CH$_3$)$_2$Si(CH$_2$)$_3$]S$_m$[(CH$_2$)$_3$Si(CH$_3$)$_2$(C$_{12}$H$_{25}$O)],
[(C$_{12}$H$_{25}$O)(CH$_3$)$_2$Si(CH$_2$)$_3$]S$_m$[(CH$_2$)$_3$Si(CH$_3$)$_2$(C$_{14}$H$_{29}$O)],
[(C$_{12}$H$_{25}$O)(CH$_3$)$_2$Si(CH$_2$)$_3$]S$_m$[(CH$_2$)$_3$Si(CH$_3$)$_2$(C$_{16}$H$_{33}$O)],
[(C$_{12}$H$_{25}$O)(CH$_3$)$_2$Si(CH$_2$)$_3$]S$_m$[(CH$_2$)$_3$Si(CH$_3$)$_2$(C$_{18}$H$_{37}$O)],
[(C$_{14}$H$_{29}$O)(CH$_3$)$_2$Si(CH$_2$)$_3$]S$_m$[(CH$_2$)$_3$Si(CH$_3$)$_2$(C$_{14}$H$_{29}$O)],
[(C$_{14}$H$_{29}$O)(CH$_3$)$_2$Si(CH$_2$)$_3$]S$_m$[(CH$_2$)$_3$Si(CH$_3$)$_2$(C$_{16}$H$_{33}$O)],
[(C$_{14}$H$_{29}$O)(CH$_3$)$_2$Si(CH$_2$)$_3$]S$_m$[(CH$_2$)$_3$Si(CH$_3$)$_2$(C$_{18}$H$_{37}$O)],
[(C$_{16}$H$_{33}$O)(CH$_3$)$_2$Si(CH$_2$)$_3$]S$_m$[(CH$_2$)$_3$Si(CH$_3$)$_2$(C$_{16}$H$_{33}$O)], p0 [(C$_{16}$H$_{33}$O)(CH$_3$)$_2$Si(CH$_2$)$_3$]S$_m$[(CH$_2$)$_3$Si(CH$_3$)$_2$(C$_{18}$H$_{37}$O)],
[(C$_{18}$H$_{37}$O)(CH$_3$)$_2$Si(CH$_2$)$_3$]S$_m$[(CH$_2$)$_3$Si(CH$_3$)$_2$(C$_{18}$H$_{37}$O)], where m=1.5-4,5.

Compounds of the general formula I where X=S and m=1.5-4.5

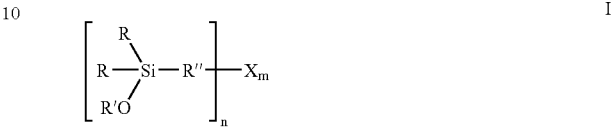

can preferably be prepared by reacting water-containing sulphurization reagents with (haloorganyl)alkoxysilanes of the general formula II

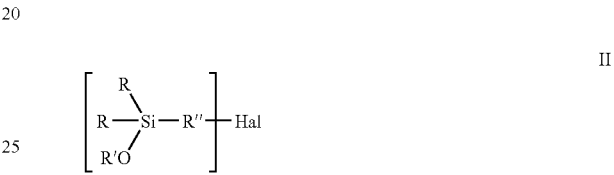

in an alcohol in a closed vessel in the absence of air and at an elevated pressure in the presence of additives.

In the preparation of organosilanes of the general formula I where X=S and m=1.5-4.5, additives may be, for example, organic or inorganic acids or organic or inorganic bases.

Organic acids may be compounds of the following parent structures: alkyl-COOH, aryl-COOH, aralkyl-COOR, alkyl-S(O)$_2$OH, HOOC-alkylene-COOH, HOOC-aryl-COOH or HOOC-aralkyl-COOH.

Organic acids may be, for example, formic acid, acetic acid, propanoic acid, pivalic acid, isooctanoic acid, isononanoic acid, lauric acid (C12), myristic acid (C14), palmitic acid (C16), stearic acid (C18), oleic acid, linoleic acid, linolenic acid, benzoic acid, oxalic acid, 1,4-cyclohexanedicarboxylic acid, adipic acid, 1,12-dodecanedioic acid, aminoundecanoic acid, phthalic acid, terephthalic acid, maleic acid, fumaric acid, malonic acid, acrylic acid or methacrylic acid.

Inorganic acids may be, for example, compounds of the composition HCl, H$_2$SO$_4$, H$_3$PO$_4$, (alkali metal ion)H$_2$PO$_4$, (alkali metal ion)$_2$HPO$_4$, H$_3$CO$_3$, (alkali metal ion)HCO$_3$ or (alkali metal ion)HSO$_4$.

In the preparation of organosilanes of the general formula I where X=S and m=1.5-4.5, acidic or basic additives which are added to the reaction mixture before, during or at the end of the process may have the structure (alkali metal ion)H$_2$P0$_1$, (alkali metal ion)$_2$HPO$_4$, (alkali metal ion)$_3$PO$_4$, (alkali metal ion)HCO$_3$, (alkali metal ion)$_2$CO$_3$, (alkali metal ion)$_2$SO$_4$ or (alkali metal ion)HSO$_4$.

Haloorganyl(halosilanes)can be used as additives in the preparation of organosilanes of the general formula I where X=S and m=1.5-4.5.

Compounds of the general formula III

((R''')$_2$HalSi—R''-Hal       III, in which Hal, R and R'' have the abovementioned meaning and R''', independently of one another, are R or Hal, can be used as (haloorganyl)halosilanes in the preparation of organosilanes of the general formula I where X=S and m=1.5-4.5.

In the preparation of organosilanes of the general formula I where $X=_{and\ m=}1.5$-$4.5$, (chloroorganyl)chlorosilanes can preferably be used as (haloorganyl)halosilanes.

In the preparation of organosilanes of the general formula I where $X=S$ and $m=1.5$-$4.5$, the abovementioned compounds can preferably be used as (haloorganyl)halosilanes.

In the preparation of organosilanes of the general formula I where $X=S$ and $m=1.5$-$4.5$, the (haloorganyl)halosilane may be a (haloorganyl)halosilane of the general formula III or a mixture of (haloorganyl)chlorosilanes of the general formula III.

Compounds which liberate inorganic or organic acids in combination with alcohols can be added as additives before and/or during and/or at the end of the reaction in the preparation of organosilanes of the general formula I where $X=S$ and $m=1.5$-$4.5$.

Compounds which liberate inorganic acids in the presence of alcohols may be chlorosilanes. Chlorosilanes may contain 1 to 4 Si—Cl bonds per silicon atom. Chlorosilanes may be $(CH_3)SiCl_3$, $(CH_3)_2SiCl_2$, $(CH_3)_3SiCl$, $SiCl_4$, $HSiCl_3$, $H_2SiCl_2$.

Compounds which liberate organic or inorganic bases in combination with alcohols may be added as additives before and/or during and/or at the end of the reaction in the preparation of organosilanes of the general formula I where $X=S$ and $m=1.5$-$4.5$.

Compounds of the general formula I where $X=S$ and $m=1.5$-$4.5$

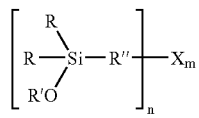

I can preferably be prepared by reacting water-containing sulphurization reagents with (haloorganyl)alkoxysilanes of the general formula II

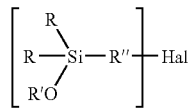

II in an alcohol in a closed vessel in the absence of air and at an elevated pressure in the presence of $H_2S$.

The amount of $H_2S$ in the preparation of organosilanes of the general formula I where $X=S$ and $m=1,5$-$4.5$ may be less than less than 500 mol %, preferably less than 100 mol %, particularly preferably less than 50 mol %, very particularly preferably less than 15 mol % based on the amount of haloorganyl(alkoxysilane) used.

In the preparation of organosilanes of the general formula I where $X=S$ and $m=1.5$-$4.5$, the yield of crude product of the process according to the invention may be greater than 80%, preferably greater than 85%, particularly preferably greater than 90%, very particularly preferably greater than 95%, based on the theoretical yield and relative to the sum of (haloorganyl)alkoxysilane and (haloorganyl)halosilane.

In the preparation of organosilanes of the general formula I where $X=S$ and $m=1.5$-$4.5$, the yield of crude product may be the gravimetrically determined sum of all liquid compounds isolated, after solvent and solids have been removed.

In the preparation of organosilanes of the general formula I where $X=S$ and $m=1.5$-$4.5$, the composition of compounds or mixtures of compounds of the general formula I where $X=S$ and $m=1.5$-$4.5$ can be influenced in an active and targeted manner by the choice of the composition of the mixtures of (haloorganyl)alkoxy-silanes, sulphurization reagents and alcohol used, the amount of alcohol and additives.

The mixture of appropriate (haloorganyl)alkoxysilane and additives used in the preparation of organosilanes of the general formula I where $X=S$ and $m=1.5$-$4.5$ can be prepared before the addition of the sulphurization reagents, depending on the apparatus used and the desired effects, some of which can be influenced independently of one another, for example selectivity of the reaction, duration of the reaction, reactor throughput, reaction of (haloorganyl)alkoxysilane and sulphurization reagent with another, value of m in $X=S_m$, reaction of alkali metal sulphide and sulphur, reaction of alkali metal hydrogen sulphide and sulphur, reaction of alkali metal hydrogen sulphide, alkali metal sulphide and sulphur, the reactor material or the process sequence.

The mixture of appropriate sulphurization reagents, sulphur and additives used in the preparation of organosilanes of the general formula I where $X=S$ and $m=1.5$-$4.5$ can be prepared before the addition of the haloorganyl(alkoxysilane), depending on the apparatus used and the desired effects, some of which can be influenced independently of one another, the reactor material or the process sequence.

The quality and type of the composition of the mixture of (haloorganyl)alkoxysilane and additives which is used in the preparation of organosilanes of the general formula I where $X=S$ and $m=1.5$-$4.5$ can be assessed on the basis of the amount and type of the hydrolysable Si-halide bonds present in the mixture.

In the preparation of organosilanes of the general formula I where $X=S$ and $m=1.5$-$4.5$, the amount of hydrolysable Si halide in the abovementioned mixtures of (haloorganyl)alkoxysilane and additives, which can be determined by said analytical method, may be between 2 and 800 000 mg/kg, preferably between 10 and 80 000 mg/kg, particularly preferably between 10 and 40 000 mg/kg, very particularly preferably between 100 and 10 000 mg/kg.

The amount of hydrolysable halide in the mixtures of haloorganyl(alkoxysilane) and additives which are used in the preparation of organosilanes of the general formula I where $X=S$ and $m=1.5$-$4.5$ is determined by the following method: 80 ml of ethanol and 10 ml of acetic acid are added to not more than 20 g of the sample in a 150 ml beaker. The halide content is titrated potentiographically with silver nitrate solution ($C(AgNO_3)=0.01$ mol/l).

In the preparation of organosilanes of the general formula I where $X=S$ and $m=1.5$-$4.5$, the advantageous molar ratios of the mixtures of (haloorganyl)alkoxy-silanes and (haloorganyl)halosilanes (additive=(haloorganyl)halosilane) may be dependent inter alia on the number of Si-halogen functions of the chosen (haloorganyl)halosilanes.

For example, in the reaction of 3-chloropropyl-(trimethoxysilane) or 3-chloropropyl(triethoxysilane) and 3-chloropropyl(trichlorosilane), a molar ratio of from 1:0.00001 to 1:0.03 can preferably be used.

For example, in the reaction of 3-chloropropyl(methyldimethoxysilane) or 3-chloropropyl(methyldiethoxy-silane) and 3-chloropropyl(methyldichlorosilane), a molar ratio of from 1:0.00001 to 1:0.045 can preferably be used.

For example, in the reaction of 3-chloropropyl-(dimethylmethoxysilane) or of 3-chloropropyl(dimethylethoxysilane)

and 3-chloropropyl(dimethylchlorosilane), a molar ratio of from 1:0.00001 to 1:0.09 can preferably be used.

In the preparation of organosilanes of the general formula I where X=S and m=1.5-4.5, the (haloorganyl)alkoxysilane and the additives can be mixed with one another in any desired sequence or manner, at any desired temperature and in any desired duration and only thereafter the alcohol and sulphurization reagents added together or in succession.

In the preparation of organosilanes of the general formula I where X=S and m=1.5-4.5, additives, sulphurization reagents and alcohol can be mixed with one another in any desired sequence or manner, at any desired temperature and in any desired duration and only thereafter the (haloorganyl) alkoxysilane added.

In the preparation of organosilanes of the general formula I where X=S and m=1.5-4.5, the (haloorganyl)-alkoxysilane, sulphurization reagents and alcohol can be mixed with one another in any desired sequence or manner, at any desired temperature and in any desired duration and only thereafter additives added.

In the preparation of organosilanes of the general formula I where X=S and m=1.5-4.5, the (haloorganyl)-alkoxysilane, sulphurization reagents and additives can be mixed with one another in any desired sequence or manner, at any desired temperature and in any desired duration and only thereafter alcohol added.

In the preparation of organosilanes of the general formula I where X=S and m=1.5-4.5, sulphurization reagents and additives can be mixed with one another in any desired sequence or manner, at any desired temperature and in any desired duration and only thereafter the alcohol and (haloorganyl)alkoxysilane added together or in succession.

In the preparation of organosilanes of the general formula I where X=S and m=1.5-4.5, water-containing sulphurization reagents which may be used are lithium hydrogen sulphide (LiSH), sodium hydrogen sulphide (NaSH), potassium hydrogen sulphide (KSH) or caesium hydrogen sulphide (CsSH).

Sulphurization reagents which can preferably be used are sodium- and potassium-containing sulphurization reagents. $Na_2S$, $Na_2S_2$, $Na_2S_3$, $Na_2S_4$, $Na_2S_5$, $K_2S$, $K_2S_2$, $K_2S_3$, $K_2S_4$ or $K_2S_5$ can particularly preferably be used.

The water-containing sulphurization reagents can be added to the reaction mixture independently of one another, before and/or during the reaction.

The water-containing sulphurization reagents can, independently of one another, be mixed with sulphur or $H_2S$ and added to the reaction mixture before, during or at the end of the reaction.

In the third embodiment, the alkali metal hydrogen sulphide may contain more than 3% by weight, preferably more than 5% by weight, particularly preferably more than 10% by weight, very particularly preferably more than 12% by weight, exceptionally preferably more than 15% by weight, of water.

In the third embodiment the $Me_2S$ may contain more than 10% by weight, preferably more than 15% by weight, particularly preferably more than 20% by weight, very particularly preferably more than 30% by weight, of water.

In the third embodiment, the $Me_2S_g$ may contain more than 10% by weight, preferably more than 1.5% by weight, particularly preferably more than 20% by weight, very particularly preferably more than 30% by weight, of water.

The water-containing sulphurization reagents used in the preparation of organosilanes of the general formula I where X=S and m=1.5-4.5 can be added to the reaction as solids or in solution.

The water-containing sulphurization reagents required for the reaction in the preparation of organosilanes of the general formula I where X=S and m=1.5-4.5 may be formed from sulphur-containing compounds before or during the reaction.

The sulphur-containing compounds from which sulphurization reagents are formed before or during the reaction in the preparation of organosilanes of the general formula I where X=S and m=1.5-4.5 may be $H_2S$, alkali metal sulphides $Me_2S$ or alkali metal polysulphides $Me_2S_g$, preferably $Li_2S$, $Na_2S$, $K_2S$, $Na_2S_2$, $Wa_2S_3$, $Na_2S_4$, $K_2S_2$, $K_2S_3$ or $K_2S_4$.

The sulphur-containing compounds from which sulphurization reagents are formed before or during the reaction can react completely or incompletely, reversibly or irreversibly, by protonation or deprotonation to give sulphurization reagents in the preparation of organosilanes of the general formula I where X=S and m=1.5-4.5.

The protonation or deprotonation of sulphur compounds from which alkali metal hydrogen sulphides are formed before or during the reaction can take place by means of additives in the preparation of organosilanes of the general formula I where X=S and m=1.5-4.5.

In the preparation of organosilanes of the general formula I where X=S and m=1.5-4.5, raw materials which contain more than 40% by weight, preferably more than 50% by weight, particularly preferably more than 60% by weight, and very particularly preferably more than 70% by weight of alkali metal hydrogen sulphide, or which contain more than 30% by weight, preferably more than 40% by weight, particularly preferably more than 50% by weight and very particularly preferably more than 59% by weight of $Me_2S$, or which contain more than 20% by weight, preferably more than 30% by weight, particularly preferably more than 40% by weight, very particularly preferably more than 50% by weight, of $Me_2S_g$ can, independently of one another, be used for the preparation of the reaction products of alkali metal hydrogen sulphide, $Me_2S$, $Me_2S_x$ and sulphur.

In the preparation of organosilanes of the general formula I where X=S and m=1.5-4.5, the water-containing sulphurization reagents may contain, in addition to water, further secondary constituents in an amount of less than 50% by weight, preferably less than 30% by weight, particularly preferably less than 20% by weight, very particularly preferably less than 10% by weight.

In the preparation of organosilanes of the general formula I where X=S and m=1.5-4.5, further secondary constituents of water-containing sulphurization reagents may be, in addition to water, independently of one another alkali metal carbonates, alkali metal bicarbonates, alkali metal hydroxides, alkali metal sulphates, alkali metal hydrogen sulphates, alkali metal thiosulphates and/or alkali metal hydrogen thiosulphates.

In the preparation of organosilanes of the general formula I where X=S and m=1.5-4.5, the molar amount of sulphurization reagent used may exceed the sum of the molar amount of the (haloorganyl)alkoxysilane used by from 1 mold to 50 mol %, preferably by from 1 to 30 mol %, particularly preferably by from 5 to 15 mol %.

In the preparation of organosilanes of the general formula I where X=S and m=1.5-4.5, amounts of sulphurization reagent which are less than the stoichiometrically required amounts can lead to an incomplete conversion. Consequently, either the product is subsequently contaminated with starting material or complicated working-up is necessary in order to separate starting materials and products from one another.

The reaction temperature which is optimum in each case with regard to the yield of desired product and utilization of reaction volume may vary with regard to type and amount depending on the structure of (haloorganyl)alkoxysilane used and of the alcohol used as solvent.

For example, in the preparation of organosilanes of the general formula I where X=S and m=1.5-4.5, a reaction temperature between 40° and 95° C., preferably between 60° and 95° C., may be advantageous with respect to reaction times, amount of by-products and pressure build-up in the case of reactions in methanol.

For example, in the preparation of organosilanes of the general formula I where X=S and m=1.5-4.5, a reaction temperature between 50° and 130° C., preferably between 75° and 130° C., may be advantageous with regard to the reaction times, amount of by-products and pressure build-up in the case of reactions in ethanol.

In the preparation of organosilanes of the general formula I where X=S and m=1.5-4.5, the closed container can preferably be a reaction vessel which is known from the prior art and makes it possible to work at pressures up to 20 bar and temperatures up to 200° C. The closed container may have a heating/cooling circulation.

In the preparation of organosilanes of the general formula I where X=S and m=1.5-4.5, the amount of by-product may be less than 20 mol %, preferably less than 15 mol %, particularly preferably less than 10 mol %, through the choice of the reaction conditions.

In the preparation of organosilanes of the general formula I where X=S and m=1.5-4.5, the amount of by-product may be less than 20% by weight, preferably less than 15% by weight, particularly preferably less than 10% by weight through the choice of the reaction conditions.

In the preparation of organosilanes of the general formula I where X=S and m=1.5-4.5, the amount of residual haloorganyl(alkoxysilane) starting material may be less than 20% by weight, preferably less than 15% by weight, particularly preferably less than 10% by weight, very particularly preferably less than 5% by weight, through the choice of the reaction conditions.

In the third embodiment, the solvent/water mixture can be removed from the crude product suspension, preferably at reduced pressure, and the suspension forming, containing the resulting organosilane of the general formula I, can be separated from the solid, preferably by centrifuging, decanting or filtration. The solvent/water mixture can be removed at a pressure of from 800 mbar to 10 mbar, preferably by distillation. The solvent/water mixture may contain ethanol.

The suspension forming may contain Me(Hal), for example NaCl, buffer salts and organosilanes of the general formula I.

The solvent can be removed from the crude product suspension, the mixture containing the organosilanes of the general formula (I) and the solid Me(Hal) can be mixed with water, containing at least one buffer, and the resulting phases can be separated.

The working-up of the crude product suspension may include a filtration and removal of solid constituents. The working-up of the crude product suspension may include a distillation and removal of volatile constituents. The working-up of the crude product suspension may include first a distillation and then a filtration. The working-up of the crude product suspension may include first a filtration and then a distillation. The working-up of the crude product suspension may include first a filtration, then a distillation and thereafter a further filtration.

The salt-containing crude product suspension present after the reaction can be worked up at atmospheric pressure or reduced pressure, preferably at a reduced pressure between 1 and 700 mbar, particularly preferably between 5 and 500 mbar, very particularly preferably between 10 and 250 mbar.

The salt-containing product suspension present after the reaction can be worked up at ambient temperature or elevated temperature, preferably between 20 and 200° C., particularly preferably between 40 and 150° C., very particularly preferably between 50 and 100° C.

During the working-up, a mixture of product and solid may form. During the working-up, a mixture of product and alcohol may form. During the working-up, a mixture of product, alcohol and water may form. During the working-up, a mixture of product and water may form. During the working-up, a mixture of product, solid and water may form. During the working-up, a mixture of product, Me(Hal), for example sodium chloride, and water may form. During the working-up, a mixture of product, Me(Hal), for example sodium chloride, alcohol and water may form.

Water may be added to a mixture of product and/or solid and/or alcohol and/or water.

The water may be added in an amount of from 1 to 200% by weight, preferably from 1 to 100% by weight, particularly preferably from 5 to 75% by weight, very particularly preferably from 5 to 50% by weight, based on the product.

The water may be demineralized water. The water may contain a buffer, for example sodium bicarbonate or sodium carbonate. The buffer content of the water may be 1% by weight-20% by weight, preferably 2% by weight-5% by weight.

The added water may have a pH between 3 and 11, preferably between 4 and 10, particularly preferably between 5 and 9, very particularly preferably between 7 and 9.

The pH of the added water can be adjusted by means of the buffer, for example $NaHCO_3$.

The solid may preferably be present in the aqueous phase. The salt Me(Hal), for example sodium chloride, may preferably be present in the aqueous phase.

The product may separate off from the salt-containing aqueous phase by phase separation. After the phase separation, the product can be separated from the salt-containing aqueous phase. After the separation of the salt-containing phase, the product can be dried.

The process according to the invention has the advantage that readily meterable, commercially available solids, for example water-containing sodium hydrogen sulphide or sodium sulphide, are used as sulphurization reagents.

The process according to the invention furthermore has the advantage that commercially available, customary, water-containing sulphurization raw materials can be used. These water-containing raw materials which are not specially prepared are advantageous compared with the alkali metal hydrogen sulphides dried by a complicated procedure (e.g. dried to <3% by weight).

One advantage is the reduced or even absent spontaneous ignitability of the sulphurization raw materials owing to the water content present. Consequently, they can be portioned, transferred and handled under air comparatively safely. This saves an additional effort and technical installations in plants and safety apparatuses. The danger for the technical operator due to smouldering fires caused by spilled alkali metal hydrogen sulphide or alkali metal sulphide $Me_2S$ and development of fumes on oxidation thereof in the air is reduced.

A further advantage is the simplification of the process and the improved energy balance of the overall process if the sulphurization raw materials do not have to be dried in vacuo at elevated temperature or prepared from alkali metal and sulphur under drastic reaction conditions.

An advantage over azeotropic drying of the sulphurization raw materials is the simplification of the process by saving a process step and dispensing with the additional use, the consumption or the working-up of a solvent acting as a water entrainer (azeotrope former).

A further advantage of the process according to the invention is that the selectivity, the conversion and the yield of crude product can be increased simply by the use of a closed reaction vessel (autoclave or the like) and the addition of small amounts of additives.

High conversions in short batch times and at temperatures which are technically easy to realize are a further advantage of the process according to the invention.

The high yields of crude liquid products which have not condensed to give polysiloxanes are a further advantage of the process according to the invention. The process according to the invention has high yields of crude liquid products in combination with high selectivity of the sulphurization reaction, for example to give mercapto compounds of the general formula I where X=SH or polysulphide compounds of the general formula I where X=S and m is from 1.5 to 4.5.

The high monomer contents of the products, detectable by 29Si-NMR analysis are a further advantage of the process according to the invention. The high dimer and trimer content in combination with low yield of crude product, as a result of the hydrolysis of the Si—O(alkyl) groups with subsequent condensation of the silanol groups formed, would have been expected.

EXAMPLES

In the preparation of the organosilanes, NaSH from ICS Wolfen GmbH comprising from 25 to 35% by weight of water, NaSH from Lanxi Daring Chem. comprising from 15 to 25% by weight of water or NaSH from Goldschmidt TIB GmbH comprising from 20 to 30% by weight of water are used.

In the preparation of organosilanes, $Na_2S$ from Tessenderlo comprising from 35 to 45% by weight of water, $Na_2S \cdot X\ H_2O$ as obtainable, for example, through Aldrich or Merck-Schuchard, having an $Na_2S$ content of from 20 to 40% by weight, or $Na_2S \cdot 3\ H_2O$ as obtainable, for example, through Aldrich or Merck-Schuchard can be used.

For assessing the reaction mixtures, the conversion is defined as the quotient of the sum of the percentages by area of 3-mercaptopropyl(triethoxysilane), $(EtO)_3Si-(CH_2)_3-S-(CH_2)_3-Si(OEt)_3$ and $(EtO)_3Si-(CH_2)_3-S_2-(CH_2)_3-Si(OEt)_3$ and the sum of the percentages by area of 3-chloropropyl(triethoxysilane), 3-mercaptopropyl(triethoxysilane), siloxane dimers of 3-mercaptopropyl(triethoxysilane) and 3-chloropropyl(triethoxysilane), $(EtO)_3Si-(CH_2)_3-S-(CH_2)_3-Si(OEt)_3$ and $(EtO)_3Si-(CH_2)_3-S_2-(CH_2)_3-Si(OEt)_3$.

For assessing the reaction mixtures, the selectivity is defined as the quotient of the percentages by area of 3-mercaptopropyl(triethoxysilane)

and the sum of the percentages by area of 3-mercaptopropyl(triethoxysilane), siloxane dimers of 3-mercaptopropyl(triethoxysilane) and 3-chloropropyl-(triethoxysilane), $(EtO)_3Si-(CH_2)_3-S-(CH_2)_3-Si(OEt)_3$ and $(EtO)_3Si-(CH_2)_3-S_2-(CH_2)_3-Si(OEt)_3$.

For assessing the reaction mixtures, the GC crude product concentration is defined as the quotient of the percentages by area of 3-mercaptopropyl(triethoxysilane)

and the percentages by area for ethanol (the solvent).

Analysis:

GC Analysis:

The GC analysis of the reaction mixtures is carried out on an HP 6890(WLD) gas chromatograph having a 30 m long DB5 column with an internal diameter of 0.53 mm and a film thickness of 1.5 μm. The detector used is a thermal conductivity detector. The temperature programme used includes the following sequences:

Start temperature 100° C.
Initial time 1 min.
20° C./min to 280° C.
Maintain at 280° C. for 10 min.

The retention times for the following components are:
at 3.3 min=$Cl-(CH_2)_3-Si(OEt)_3$
at 5.7 min Si263=$HS-(CH_2)_3-Si(OEt)_3$
at 9.0-10.5 min various siloxane dimers from starting material silane and product silane
at 11.0 min=$(EtO)_3Si-(CH_2)_3-S-(CH_2)_3-Si(OEt)_3$
at 12.4 min=$(EtO)_3Si-(CH_2)_3-S_2-(CH_2)_3-Si(OEt)_3$ The GC analysis of the crude products isolated is carried out on a gas chromatograph (FID) using dodecane or toluene as an internal standard.

The gas chromatographic investigations of Examples 5-11 are carried out as described in "Standard Test Method for Silanes used in Rubber Formulations (Bis-(triethoxysilylpropyl)sulphanes): Characterization by Gas Chromatography (GC), D 6843-021".

HPLC Analysis:

The method for HPLC measurement is described in "Luginsland, H-D., Reactivity of the Sulfur Functions of the Disulfane Silane TESPD and Tetrasulfane Silane TESPT, paper presented at the ACS Meeting, April 1999, Chicago".

The average sulphur chain length is calculated as follows:

$$\overline{S} = \frac{\sum_{i=2}^{10} i \cdot A_i \cdot R_i / M_i}{\sum_{i=2}^{10} A_i \cdot R_i / M_i}$$

$\overline{S}$=average sulphur chain length
i=number of sulphur atoms in the silane component
$M_i$=molar mass of the silane component with i sulphur atoms
$A_i$=area of the signal of the silane component with i sulphur atoms
$R_i$=response factor of the sulphur silane component with i sulphur atoms If organosilanes of the formula I where X=S contain compounds with $S_1$, the average sulphur chain length is corrected taking into account the molecular weights.

$^{29}$Si-NMR:

The Si spectra are recorded on a Bruker Avance 500-NMR spectrometer with a measuring frequency for Si of 99.35 MHz (H-NMR 500.13 MHz). The spectra are referenced internally against tetramethylsilane (TMS=0 ppm). The samples are measured as an approx. 30% solution in $CDCl_3$ with addition of chromium acetylacetonate (about 0.05 to 0.1 molar solution) as a relaxation accelerator. The pulse frequency used is an inverse gated sequence with proton decoupling only during the acquisition time and a relaxation delay of 5 s.

| Si-29-NMR data: | |
|---|---|
| ppm | Assignment |
| −46 | R—Si(OR')3 |
| −53 | R—Si(OR')2—O—Si |
| −62 | Si—O—Si(R)(OR')—O—Si |

Correction of the Integrals:
Trimer=integral(−62 ppm)
Dimer=(integral(−53 ppm)−2·integral(−63 ppm))/2
Monomer=(integral(−46 ppm)−3·integral(−62 ppm)−2·(integral (−53 ppm)−2·integral(−62 ppm))/2)/2

The corrected integrals are directly proportional to the mole fractions of the monomers, dimers and trimers in the sample.

Example 1 (X=SH)

50 g of NaSH (70% strength with 25% by weight of water) and 750 ml of ethanol are initially introduced at room temperature into a four-necked flask heatable by means of an oil bath and are stirred for 15 min at 50° C. 150 g of 3-chloropropyl(triethoxysilane) and a further 150 ml of ethanol are added to the suspension. The mixture is heated with stirring and refluxed for 180 min. The mixture is then cooled to about 55° C. and 1 g of formic acid is metered in. After 15 min, a sample is taken and analysed by gas chromatography.

The GC analysis of the reaction mixture gives the following composition in percent by area:

| | |
|---|---|
| Ethanol | 96.424 |
| 3-Chloropropyl(triethoxysilane) | 0.086 |
| 3-Mercaptopropyl(triethoxysilane) | 1.828 |
| Siloxane dimers from starting material silane and product silane | 0.322 |
| $(EtO)_3Si$—$(CH_2)_3$—S—$(CH_2)_3$—$Si(OEt)_3$ | 0.322 |
| $(EtO)_3Si$—$(CH_2)_3$—$S_2$—$(CH_2)_3$—$Si(OEt)_3$ | 0 |

Based on the abovementioned values, the conversion is >96% and the selectivity of the reaction is 74%. Based on the abovementioned values, the GC crude product concentration is 1.9%.

The suspension obtained is filtered. The filtrate obtained is treed from the volatile constituents at 20-600 mbar and 60-80° C. on a rotary evaporator. 47.4 g of a colourless, insoluble solid are obtained.

Example 2 (X=SH)

60.9 g of NaSH (70% strength with 25% by weight of water) and 750 ml of ethanol are initially introduced at room temperature into a four-necked flask heatable by means of an oil bath and stirred for 15 min at 50° C. A mixture of 7.5 g of 3-chloropropyl(trichlorosilane) and 150 g of 3-chloropropyl(triethoxysilane) is added by means of a pressure burette. A further 150 ml of ethanol are added to the suspension. The mixture is heated with stirring and refluxed for 180 min. The mixture is then cooled to about 55° C. and 1 g of formic acid is metered in. After 15 min, a sample is taken and analysed by gas chromatography. The GC analysis of the reaction mixture gives the following composition in percent by area:

| | |
|---|---|
| Ethanol | 97.973 |
| 3-Chloropropyl(triethoxysilane) | 0.021 |
| 3-Mercaptopropyl(triethoxysilane) | 1.042 |
| Siloxane dimers from starting material silane and product silane | 0.133 |
| $(EtO)_3Si$—$(CH_2)_3$—S—$(CH_2)_3$—$Si(OEt)_3$ | 0.142 |
| $(EtO)_3Si$—$(CH_2)_3$—$S_2$—$(CH_2)_3$—$Si(OEt)_3$ | 0.009 |

Based on the abovementioned values, the conversion is >98% and the selectivity of the reaction is 79%. Based on the abovementioned values, the GC crude product concentration is 1.1%.

The suspension obtained is filtered. The filtrate obtained is freed from the volatile constituents on a rotary evaporator at 20-600 mbar and 60-80° C. 40 g of a colourless, insoluble, highly viscous product are obtained.

Example 3 (X=SH)

50 g of NaSH (70% strength with 25% by weight of water) and 750 ml of ethanol are initially introduced at room temperature into an autoclave having a glass double jacket and Hastelloy C22 cover+fittings (Buechi AG) and stirred for 15 min at 50° C. 150 g of 3-chloropropyl(triethoxysilane) are added by means of a pressure burette. A further 150 ml of ethanol are added to the suspension. The mixture is heated to 105-110° C. with stirring and the temperature is maintained for 180 min. The mixture is then cooled to approximately 55° C. and 1 g of formic acid is metered in. After 15 min, a sample is taken and analysed by gas chromatography. The GC analysis of the reaction mixture gives the following composition in percent by area:

| | |
|---|---|
| Ethanol | 91.611 |
| 3-Chloropropyl(triethoxysilane) | 0.195 |
| 3-Mercaptopropyl(triethoxysilane) | 5.659 |
| Siloxane dimers from starting material silane and product silane | 0.829 |
| $(EtO)_3Si$—$(CH_2)_3$—S—$(CH_2)_3$—$Si(OEt)_3$ | 0.253 |
| $(EtO)_3Si$—$(CH_2)_3$—$S_2$—$(CH_2)_3$—$Si(OEt)_3$ | 0.033 |

Based on the abovementioned values, the conversion is >97% and the selectivity of the reaction is 84%. Based on the abovementioned values, the GC crude product concentration is 6.2%.

The suspension obtained is filtered. The filtrate obtained is freed from the volatile constituents on a rotary evaporator at 20-600 mbar and 60-80° C. The precipitated solid is separated off by filtration. 85.2 g of a colourless liquid are obtained. The yield of crude product is 57.4%.

The analysis by gas chromatography (dodecane as internal standard) gives the following composition of the crude product obtained, in percent by weight (% by weight):

| | |
|---|---|
| 3-Chloropropyl(triethoxysilane) (GC) | 1.8 |
| 3-Mercaptopropyl(triethoxysilane) (GC) | 52.2 |
| $(EtO)_3Si$—$(CH_2)_3$—S—$(CH_2)_3$—$Si(OEt)_3$ (GC) | 2.2 |

Example 4 (X=SH)

60.9 g of NaSH (70% strength with 25% by weight of water) and 750 ml of ethanol are initially introduced at room temperature into an autoclave having a glass double jacket and Hastelloy C22 cover+fittings (Buechi AG) and stirred for 15 min at 50° C. A mixture of 7.5 g of 3-chloropropyl(trichlorosilane) and 150 g of 3-chloropropyl(triethoxysilane) is added by means of a pressure burette. A further 150 ml of ethanol are added to the suspension. The mixture is heated to 105-110° C. with stirring and the temperature is maintained for 180 min. The mixture is then cooled to approximately 55° C. and 1 g of formic acid is metered in. After 15 min, a sample is taken and analysed by gas chromatography. The GC analysis of the reaction mixture gives the following composition in percent by area:

| | |
|---|---|
| Ethanol | 84.203 |
| 3-Chloropropyl(triethoxysilane) | 0.057 |
| 3-Mercaptopropyl(triethoxysilane) | 12.591 |
| Siloxane dimers from starting material silane and product silane | 0.349 |
| $(EtO)_3Si—(CH_2)_3—S—(CH_2)_3—Si(OEt)_3$ | 0.232 |
| $(EtO)_3Si—(CH_2)_3—S_2—(CH_2)_3—Si(OEt)_3$ | 0.179 |

Based on the abovementioned values, the conversion is >99% and the selectivity of the reaction is 94%. Based on the abovementioned values the GC crude product concentration is 14.9%.

The suspension obtained is filtered. The filtrate obtained is freed from the volatile constituents on a rotary evaporator at 20-600 mbar and 60-80° C. The precipitated solid is separated off by filtration. 141.7 g of a colourless liquid are obtained. The yield of crude product is 90.3%. The liquid obtained has a residual water content of 0.3% by weight.

The analysis by gas chromatography (dodecane as internal standard) gives the following composition of the crude product obtained, in percent by weight (% by weight):

| | |
|---|---|
| 3-Chloropropyl(triethoxysilane) (GC) | 0.4 |
| 3-Mercaptopropyl(triethoxysilane) (GC) | 77.6 |
| $(EtO)_3Si—(CH_2)_3—S—(CH_2)_3—Si(OEt)_3$ (GC) | 1.5 |

Example 5 (X=S and m=2.1)

300 g of ethanol, 96.7 g of $K_2CO_3$, 33.6 g of $NaHCO_3$, 37.1 g of elemental sulphur and 63.3 g of NaSH hydrate (71% strength, contains 25% by weight of water) are initially introduced at room temperature into an autoclave having a glass double jacket and Hastelloy C22 cover+fittings (Buechi AG) and heated to 80° C. After 30 min, 500 g of 3-chloropropyl (triethoxysilane) are added slowly. The pressure in the reactor increases to 3.5 bar. After 20 min, 13.15 g of $Na_2S$ hydrate (water content of 36% by weight) are added. This addition is repeated 3 times so that the total amount of $Na_2S$ hydrate is 52.6 g. After a further 30 min, cooling is effected and the salt is separated off and washed with ethanol. The solvent is removed from the product under reduced pressure at about 80-110° C.

A slightly yellow, liquid product having a crude yield of 93% is obtained.

The GC, HPLC and 29—Si-NMR analyses give the following values:

| | |
|---|---|
| 3-Chloropropyl(triethoxysilane)/GC | 2.9% by weight |
| 3-Mercaptopropyl(triethoxysilane)/GC | 2.1% by weight |
| $(EtO)_3Si—(CH_2)_3—S—(CH_2)_3—Si(OEt)_3$/GC | 0.1% by weight |
| Average sulphur chain length $S_m$/HPLC + GC | 2.2 |
| Monomer content/$^{29}$Si-NMR | 93.0% by weight |

Example 6 (S=X and m=2.7)

300 g of ethanol, 37.0 g of elemental sulphur and 63.2 g of NaSH hydrate (71% strength, contains 25% by weight of water) are initially introduced at room temperature into an autoclave having a glass double jacket and Hastelloy C22 cover+fittings (Buechi AG) and heated to 80° C. After 30 min, 500 g of 3-chloro-propyl(triethoxysilane) are added slowly. The pressure in the reactor increases to 3.5 bar. After 20 min, 13.3 g of $Na_2S$ hydrate (water content 36% by weight) are added. This addition is repeated 3 times so that altogether 53.2 g of $Na_2S$ hydrate are present in the reaction mixture. After a further 30 min, cooling is effected and the salt is separated off and washed with ethanol. The solvent is removed from the product under reduced pressure at about 80-110° C.

A slightly yellow, liquid product having a crude yield of 98% is obtained.

The GC, HPLC and 29—Si-NMR analyses give the following values:

| | |
|---|---|
| 3-Chloropropyl(triethoxysilane)/GC | 14.6% by weight |
| 3-Mercaptopropyl(triethoxysilane)/GC | 7.8% by weight |
| $(EtO)_3Si—(CH_2)_3—S—(CH_2)_3—Si(OEt)_3$/GC | 0.1% by weight |
| Average sulphur chain length $S_m$/HPLC + GC | 2.7 |
| Monomer content/$^{29}$Si-NMR | 100% by weight |

Example 7 (X=S with m=3.7)

300 g of ethanol, 100.0 g of elemental sulphur and 33.7 g of NaSH hydrate (71% strength, contains 25% by weight of water) are initially introduced together with 96.7 g of $K_2CO_3$ and 33.6 g of $NaHCO_3$ at room temperature into an autoclave having a glass double jacket and Hastelloy C22 cover+fittings (Buechi AG) and heated to 80° C. After 30 min, 500 g of 3-chloropropyl-(triethoxysilane) are added slowly. The pressure in the reactor increases to 3.5 bar. After 20 min, 17.6 g of $Na_2S$ hydrate (water content 36% by weight) are added. This addition is repeated 3 times so that altogether 70.4 g of $Na_2S$ hydrate are present in the reaction mixture. After a further 30 min, cooling is effected and the salt is separated off and washed with ethanol. The solvent is removed from the product under reduced pressure at about 80-110° C.

A red, liquid product having a crude yield of 98% is obtained.

The GC, HPLC and 29—Si-NMR analyses give the following values:

| | |
|---|---|
| 3-Chloropropyl(triethoxysilane)/GC | 3.4% by weight |
| 3-Mercaptopropyl(triethoxysilane)/GC | 1.6% by weight |
| $(EtO)_3Si—(CH_2)_3—S—(CH_2)_3—Si(OEt)_3$/GC | 0.0% by weight |
| Average sulphur chain length/HPLC + GC | 3.7 |
| Monomer content/$^{29}$Si-NMR | 98% by weight |

Example 8 (X=S and m=2.67)

251 g of ethanol, 18.6 g of elemental sulphur, 35.9 g of NaSH hydrate (71% strength, contains 25% by weight of water), 48.5 g of $K_2CO_3$ and 16.9 g of $NaHCO_3$ are initially introduced at room temperature into a 3-necked flask having a stirrer, thermometer and reflux condenser and heated to 80° C. After 30 min, 250 g of 3-chloropropyl(triethoxysilane) are added slowly. After 60 min, cooling is effected and the salt is separated off and washed with ethanol. The solvent is removed from the product under reduced pressure at about 80-110° C.

A yellow, liquid product having a crude yield of 98% is obtained.

The $^1$H- and $^{29}$Si-NMR analyses give the following values:

| | |
|---|---|
| 3-Chloropropyl(triethoxysilane)/GC | 35.9% by weight |
| 3-Mercaptopropyl(triethoxysilane)/GC | 0.0% by weight |
| $(EtO)_3Si$—$(CH_2)_3$—S—$(CH_2)_3$—$Si(OEt)_3$/GC | 0.0% by weight |
| Average sulphur chain length $S_m$/HPLC | 2.67 |
| Monomer content/$^{29}$Si-NMR | 92.1% by weight |

Example 9 (X=S and m=3.6)

481 g (2 mol) of DYNASYLAN CPTEO (CPTEO: 3-chloro-propyltriethoxysilane from Degussa AG), 88 g (2.75 mol) of sulphur, 120 ml of ethanol, 5 g of $NaHCO_3$ and 5 g of $Na_2CO_3$ are initially introduced and stirred at 65° C.-70° C. 132 g (2 mol) of $Na_2S \cdot 3H_2O$ (Tessenderlo Chemie Belgium, water content about 36% by weight) are added in 4 portions to the batch in the course of one hour. A slight increase in the reaction temperature is observed after addition of the $Na_2S \cdot 3H_2O$, which is finely comminuted beforehand. The batch becomes deep red.

One hour after the last portion of $Na_2S \cdot 3H_2O$ is added, the first sample is taken and investigated by GC. The reaction mixture still contains 12.2% by weight of CPTEO. The CPTEO content has decreased to 5.6% by weight after a further hour and to 3.2% by weight after 3 hours. After a reaction time of four hours, the CPTEO content in the reaction mixture is still 2.1% by weight (altogether about 20 g of reaction mixture are taken for GC analyses). The reaction mixture has a yellow-orange colour after four hours.

The ethanol and water are distilled off on a rotary evaporator (pressure from about 200 mbar to <1 mbar, bath temperature from 25° C. to 100° C.). 130 g of distillate (water content 37%=48 g of water) are obtained.

The salt is separated off by filtration and washed twice with cyclohexane and once with ethanol.

After the removal of the solvent, 497 g of a yellow product having the following analytical data are obtained:

| | |
|---|---|
| 3-Chloropropyl(triethoxysilane)/GC | 1.5% by weight |
| Average sulphur chain length $S_m$/HPLC | 3.6 |
| Monomer content/$^{29}$Si-NMR | 98.4% by weight |

Example 10 (X=S and m=3.73)

The following substances are initially introduced into a 1 liter reactor:
  481 g (2 mol) of CPTEO,
  91 g (2.85 mol) of sulphur powder,
  120 ml of ethanol,
  5 g of $NaHCO_3$ and
  5 g of $NaCO_3$—.

The reactor content is then heated to 50° C. 132 g (2 mol) of $Na_2S \cdot 3H_2O$ (finely comminuted, water content about 36% by weight) are then added in 4 portions to the reaction mixture with stirring in the course of ½ an hour. During this addition a slight increase in temperature in the reactor is found.

After the end of the addition of $Na_2S \cdot 3H_2O$, the reactor content is stirred for 3 hours at 68° C. to complete the reaction.

The GC analyses of the reaction mixture give a CPTEO content of 2.3%.

Without cooling, the reaction mixture is transferred to a rotary evaporator and the ethanol and water are separated off. 80% of the amount of ethanol/water are distilled off at a pressure of 400 mbar and a temperature of from 70 to 96° C. The remaining 20% of the amount of ethanol/water are distilled off at a pressure of from 400 mbr to 1 mbar and a temperature of 96° C.

The Si 69/NaCl mixture in the reactor is cooled to 50° C. and 330 ml of buffered demineralized water (2% of $NaHCO_3$) are then added in the course of 5 minutes in order to dissolve the NaCl.

The phase separation takes place immediately after the stirrer is switched off.

The water content of the organic phase (slightly green colour detectable) is 2800 ppm, Thereafter, the organic phase is dried in a rotary evaporator (pressure 1 mbar, temperature 96° C.) and then filtered. 488 g of a yellow product are obtained.

Analytical values from GC, HPLC and 29Si-NMR for the end product:

| | |
|---|---|
| 3-Chloropropyl(triethoxysilane)/GC | 1.7% by weight |
| Average sulphur chain length $S_m$/HPLC | 3.73 |
| Monomer content/$^{29}$Si-NMR | 94.1% by weight |

Example 11 (X=S and m=3.74)

The following substances are initially introduced into a 1 liter reactor:
  481 g (2 mol) of CPTEO
  91 g (2.85 mol) of sulphur powder
  120 ml of azeotrope ethanol (95% of ethanol, 5% of water)
  5 g of $NaHCO_3$
  5 g of $NaCO_3$.

The reactor content is then heated to 50° C. 132 g (2 mol) of $Na_2S \cdot 3H_2O$ (finely comminuted, water content about 36% by weight) are then added in 4 portions to the reaction mixture with stirring in the course of ½ an hour. During this addition a slight increase in temperature in the reactor is found.

After the end of the addition of $Na_2S \cdot 3H_2O$, the reactor content is stirred for 3 hours at 68° C. to complete the reaction.

The GC analyses of the reaction mixture give a CPTEO content of 2.5%.

Without cooling, the reaction mixture is then transferred to a rotary evaporator and the ethanol and water are separated off. 80% of the amount of ethanol/water are distilled off at a pressure of 400 mbar and a temperature of from 70 to 96° C. The remaining 20% of the amount of ethanol/water are distilled off at a pressure of from 400 mbar to 1 mbar and a temperature of 96° C.

The Si69/NaCl mixture in the reactor is then cooled to 50° C. and 330 ml of buffered demineralized water (2% of $NaHCO_3$) are then added in the course of 5 minutes in order to dissolve the NaCl.

The phase separation takes place immediately after the stirrer is switched off.

The water content of the organic phase (slightly green colour detectable) is about 2800 ppm.

Thereafter, the organic phase is dried in a rotary evaporator (pressure 1 rmbar, temperature 96° C.) and then filtered. 489 g of a yellow product are obtained.

Analytical values from GC, HPLC and 29Si-NMR for the end product:

| | |
|---|---|
| 3-Chloropropyl(triethoxysilane)/GC | 2.0% by weight |
| Average sulphur chain length $S_m$/HPLC | 3.74 |
| Monomer content/$^{29}$Si-NMR | 91.0% by weight |

Example 12 (X=S and m=2.16)

200 g of ethanol (contains 7.5% of $H_2O$), 55.0 g of $Na_2CO_3$, 5.0 g of $NaHCO_3$, 25.0 g of $Na_2S$ hydrate (61% strength, contains 37% of $H_2O$), 26.4 g of elemental sulphur and 66.05 g of NaSH hydrate (71% strength, contains 29% of $H_2O$) are initially introduced at room temperature into an autoclave having a glass double jacket and Hastelloy C22 cover+fittings (Buechi AG) and heated to 68° C. in the closed system. The pressure in the reactor increases. After 20 min, the 3-chloro-propyltriethoxysilane is metered in slowly so that the reaction temperature does not exceed 70° C. After the end of the metering, thermostating at 8° C. is effected for 120 min. Thereafter, cooling is effected, the superatmospheric pressure is released and the salt is separated off and washed with ethanol. The solvent is removed from the product under reduced pressure at about 70° C.

A slightly yellow product having a crude yield of 94% is obtained.

The GC, HPLC and 29-Si-NMR analyses give the following values:

| | |
|---|---|
| 3-Chloropropyl(triethoxysilane)/GC | 1.9% by weight |
| 3-Mercaptopropyl(triethoxysilane)/GC | 1.6% by weight |
| $(EtO)_3Si$—$(CH_2)_3$—S—$(CH_2)_3$—$Si(OEt)_3$/GC | 0.3% by weight |
| Average sulphur chain length/HPLC + GC | 2.16 |
| Monomer content/$^{29}$Si-NMR | 100% by weight |

Example 13 (X=S and m=3.71)

150 g of ethanol (contains 7.5% of $H_2O$), 34.0 g of $Na_2CO_3$, 55.0 g of $Na_2S$ hydrate (61% strength, contains 37% of $H_2O$), 68.0 g of elemental sulphur and 25.75 g of NaSH hydrate (71% strength, contains 29% of $H_2O$) are initially introduced at room temperature into an autoclave having a glass double jacket and Hastelloy C22 cover+fittings (Buechi AG) and heated to 68° C. in the closed system. The pressure in the reactor increases. After 20 min, the 3-chloro-propyltriethoxysilane is metered in slowly so that the reaction temperature does not exceed 70° C. After the and of the metering, thermostating at 74° C. is effected for 120 min. Thereafter, cooling is effected, the superatmospheric pressure is released and the salt is separated off and washed with ethanol. The solvent is removed from the product under reduced pressure at about 70° C.

A slightly yellow product having a crude yield of 94.5% is obtained.

The GC, HPLC and 29-Si-NMR analyses give the following values;

| | |
|---|---|
| 3-Chloropropyl(triethoxysilane)/GC | 2.5% by weight |
| 3-Mercaptopropyl(triethoxysilane)/GC | 0.2% by weight |
| $(EtO)_3Si$—$(CH_2)_3$—S—$(CH_2)_3$—$Si(OEt)_3$/GC | 0.1% by weight |
| Average sulphur chain length/HPLC + GC | 3.71 |
| Monomer content/$^{29}$Si-NMR | 97.2% by weight |

Example 14 (X=S and m=3.62)

150 g of ethanol (contains 7.5% of $H_2O$), 34.0 g of $Na_2CO_3$, 55.0 g of $Na_2S$ hydrate (61% strength, contains 37% of $H_2O$), 68.0 g of elemental sulphur and 25.75 g of NaSH hydrate (71% strength, contains 29% of $H_2O$) are initially introduced at room temperature into an autoclave having a glass double jacket and Hastelloy C22 cover+fittings (Buechi AG) and heated to 68° C. in the closed system. The pressure in the reactor increases. After 20 min, the 3-chloro-propyltriethoxysilane is metered in slowly so that the reaction temperature does not exceed 70° C. After the end of the metering, thermostating at 74° C. is effected for 120 min. Thereafter, cooling is effected, the superatmospheric pressure is released and the salt is separated off and washed with ethanol. The solvent is removed from the product under reduced pressure at about 70° C.

A slightly yellow product having a crude yield of 94% is obtained.

The GC, HPLC and 29-Si-NMR analyses give the following values;

| | |
|---|---|
| 3-Chloropropyl(methyldiethoxysilane)/GC | 4.0% by weight |
| Average sulphur chain length/HPLC + GC | 3.62 |

Example 15 (X=SH)

52 g of NaSH (70% strength with 25% by weight of water) are initially introduced at room temperature with 500 ml of ethanol (Seccosolv quality, not more than 0.02% of water) into an autoclave having a glass double jacket and Hastelloy C22 cover+fittings (Buechi AG) and the autoclave is closed. The suspension is heated to 55° C. for 20 minutes. A mixture of 100 g of 3-chloropropyl(dimethylethoxysilane) and 5 g of 3-chloropropyl(dimethylchlorosilane) is metered into the suspension by means of a pump. A further 300 ml of ethanol (Seccosolv quality, not more than 0.02% of water) are then added to the mixture by means of a pump. The mixture is heated to 93° C. with stirring and the temperature is maintained for 180 min. The mixture is then cooled and the autoclave is opened. The reactor content is discharged and filtered. The filter cake is washed with toluene. The GC analysis of the crude product gives the following constituents in % by area:

| | |
|---|---|
| Ethanol | 79.1 |
| Toluene | 15.5 |
| 3-Chloropropyl(dimethylethoxysilane) | 0.5 |
| 3-Mercaptopropyl(dimethylethoxysilane) | 3.5 |
| Siloxane dimer | 0.03 |
| $(EtO)_3Si-(CH_2)_3-S_x-(CH_2)_3-Si(OEt)_3$ | 0.2 |

Based on the abovementioned values, the conversion is 88% and the selectivity of the reaction is 94%.

The filtrate is freed from the solvent on a rotary evaporator. The residue is taken up with toluene and filtered. The filter cake is washed thoroughly with toluene and the filtrate is freed from the solvent on a rotary evaporator. 82.5 g of liquid end product are obtained.

Example 16 (X=SH)

59.4 g of NaSH (70% strength with 25% by weight of water) are initially introduced at room temperature with 500 ml of ethanol into an autoclave having a glass double jacket and Hastelloy C22 cover+fittings (Buechi AG) and the autoclave is closed. The suspension is heated to 50° C. for 15 minutes. A mixture of 100 g of 3-chloropropyl(dimethylethoxysilane) and 15 g of 3-chloropropyl(dimethylchlorosilane) is metered into the suspension by means of a pump. A further 100 ml of ethanol are then added to the mixture by means of a pump. The mixture is heated to 95° C. with stirring and the temperature is maintained for 150 min. The mixture is then cooled and the autoclave opened. The reactor content is discharged, 1.4 g of formic acid are added, stirring is effected for 15 min and filtration is then carried out. The filter cake is washed with ethanol and the filtrate is freed from the solvent on a rotary evaporator. 108.7 g of liquid end product are isolated.

Example 17 (X=SH)

180 g of NaSH (70% strength with 24% by weight of water) are initially introduced at room temperature with 300 g of ethanol and 25 g of acetic acid into an autoclave having a glass double jacket and Hastelloy C22 cover+fittings (Buechi AG) and the autoclave is closed. The suspension is heated to 50° C. for 15 minutes. 317 g of 3-chloropropyl(methyldiethoxysilane) are metered into the suspension by means of a pump. The mixture is heated to 73° C. with stirring and the temperature is maintained for 180 min. The mixture is then cooled to 50° C. and the autoclave is opened. The GC analysis of the crude product gives the following composition in percent by area:

| | |
|---|---|
| Ethanol | 38.1 |
| 3-Chloropropyl(methyldiethoxysilane) | 0.9 |
| 3-Mercaptopropyl(methyldiethoxysilane) | 48.4 |

Based on the abovementioned values, the conversion is 98%.

The reactor content is discharged, mixed with 400 g of pentane and filtered. The filter cake is washed with pentane. 1113 g of filtrate are obtained.

The filtrate obtained is neutralized with acetic acid. The product solution obtained is freed from the volatile constituents on a rotary evaporator at 20-600 mbar and 60-80° C. The precipitated solid is separated off by filtration. 251.4 g of a colourless liquid are obtained.

Example 18 (X=SH)

100 g of NaSH (71% strength with 24% by weight of water) are initially introduced at room temperature with 400 g of ethanol (water content 5% by weight) and 18 g of acetic acid into an autoclave having a glass double jacket and Hastelloy C22 cover+fittings (Buechi AG) and the autoclave is closed. The suspension is heated to 50° C. for 15 minutes. 240 g of 3-chloropropyl(triethoxysilane) are metered into the suspension by means of a pump. The mixture is heated to 80° C. with stirring and the temperature is maintained for 180 min. The mixture is then cooled to 51° C. and the autoclave is opened. The reactor content is discharged and filtered. The filter cake is washed with ethanol (water content 5% by weight). 1049.9 g of filtrate are obtained. The GC analysis of the filtrate gives the following constituents in % by weight (internal standard is toluene):

| | |
|---|---|
| Ethanol | 55.1 |
| 3-Chloropropyl(triethoxysilane) | 2.1 |
| 3-Mercaptopropyl(triethoxysilane) | 16.4 |
| $(EtO)_3Si-(CH_2)_3-S-(CH_2)_3-Si(OEt)_3$ | 0.2 |
| $(EtO)_3Si-(CH_2)_3-S_2-(CH_2)_3-Si(OEt)_3$ | 2.1 |

Based on the abovementioned values (% by weight), the conversion is 90% and the selectivity of the reaction is 88%. The crude product yield is 95%, based on the abovementioned values.

Example 19 (X=SH)

100 g of NaSH (71% strength with 24% by weight of water) are initially introduced at room temperature with 400 g of ethanol (water content 5% by weight), 46 g of $NaHCO_3$, 5.05 g of $Na_2CO_3$ and 18 g of acetic acid into an autoclave having a glass double jacket and Hastelloy C22 cover+fittings (Buechi AG) and the autoclave is closed. The suspension is heated to 51° C. for 15 minutes. 240 g of 3-chloropropyl-(triethoxysilane) are metered into the suspension by means of a pump. The mixture is heated to 81° C. with stirring and the temperature is maintained for 90 min. The mixture is then cooled to 51° C. and the autoclave is opened. The reactor content is discharged and filtered. The filter cake is washed with ethanol (water content 5% by weight). 1081.2 g of filtrate are obtained. The GC analysis of the filtrate gives the following constituents in % by weight (internal standard is toluene):

| | |
|---|---|
| Ethanol | 54 |
| 3-Chloropropyl(triethoxysilane) | 2.2 |
| 3-Mercaptopropyl(triethoxysilane) | 15.7 |
| $(EtO)_3Si-(CH_2)_3-S-(CH_2)_3-Si(OEt)_3$ | 0.2 |
| $(EtO)_3Si-(CH_2)_3-S_2-(CH_2)_3-Si(OEt)_3$ | 2.9 |

Based on the abovementioned values (% by weight), the conversion is 89% and the selectivity of the reaction is 83.5%. The crude product yield is 95%, based on the abovementioned values.

Example 20 (X=SH)

100 g of NaSH (71% strength with 24% by weight of water) are initially introduced at room temperature with 400 g of ethanol (water content 5% by weight), 46 g of NaHCO$_3$, 5.05 g of Na$_2$CO$_3$ and 18 g of acetic acid into an autoclave having a glass double jacket and Hastelloy C22 cover+fittings (Buechi AG) and the autoclave is closed. The suspension is heated to 51° C. for 15 minutes. 240 g of 3-chloropropyl-(triethoxysilane) are metered into the suspension by means of a pump. The mixture is heated to 81° C. with stirring and the temperature is maintained for 120 min. The mixture is then cooled to 44° C. and the autoclave is opened. The reactor content is discharged and filtered. The filter cake is washed with ethanol (water content 5% by weight). 1052.9 g of filtrate are obtained. The GC analysis of the filtrate gives the following constituents in % by weight (internal standard is toluene):

| | |
|---|---|
| Ethanol | 52.4 |
| 3-Chloropropyl(triethoxysilane) | 1 |
| 3-Mercaptopropyl(triethoxysilane) | 16.8 |
| (EtO)$_3$Si—(CH$_2$)$_3$—S—(CH$_2$)$_3$—Si(OEt)$_3$ | 0.2 |
| (EtO)$_3$Si—(CH$_2$)$_3$—S$_2$—(CH$_2$)$_3$—Si(OEt)$_3$ | 0.9 |

Based on the abovementioned values (% by weight), the conversion is 95% and the selectivity of the reaction is 94%.

Example 21 (X=SH)

100 g of NaSH (71% strength with 24% by weight of water) are initially introduced at room temperature with 400 g of ethanol, 23 g of Na$_2$HPO$_4$·2H$_2$O, 17 g of KH$_2$POC and 18 g of acetic acid into an autoclave having a glass double jacket and Hastelloy C22 cover+fittings (Buechi AG) and the autoclave is closed. The suspension is heated for 15 minutes. 240 g of 3-chloropropyl(triethoxysilane) are metered into the suspension by means of a pump at between 40 and 50° C. The mixture is heated to 89° C. with stirring and the temperature is maintained for 90 min. The mixture is then cooled to 50° C. and the autoclave is opened. The reactor content is discharged and filtered. The filter cake is washed with ethanol. 1109.2 g of filtrate are obtained. The GC analysis of the filtered crude product solution gives, in % by weight (internal standard is toluene):

| | |
|---|---|
| Ethanol | 57.4 |
| 3-Chloropropyl(triethoxysilane) | 2.2 |
| 3-Mercaptopropyl(triethoxysilane) | 14.3 |
| (EtO)$_3$Si—(CH$_2$)$_3$—S—(CH$_2$)$_3$—Si(OEt)$_3$ | 0.3 |
| (EtO)$_3$Si—(CH$_2$)$_3$—S$_2$—(CH$_2$)$_3$—Si(OEt)$_3$ | 2.8 |

In the crude product of the reaction, >90% by weight of the silane used is present in unhydrolysed form.

Based on the values stated in the table (% by weight), the conversion is 89% and the selectivity of the reaction is 82%.

We claim:

1. Process for the preparation of an organosilane of the formula I,

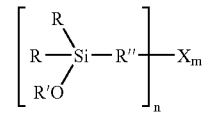

in which
R are identical or different and are a C$_1$-C$_8$-alkyl group, C$_1$-C$_8$-alkenyl, C$_1$-C$_8$-aryl or C$_1$-C$_8$-aralkyl group or an OR' group, R' are identical or different and are a branched or straight-chain monovalent C$_1$-C$_{24}$-alkyl or -alkenyl group, an aryl group, an aralkyl group, a hydrogen (—H), an alkyl ether group O—(CR$^{111}_2$)—O-Alk or 0-(CR$^{III}_2$)$_y$—O-Alk or an alkyl polyether group 0-(CR$^{III}$20)y-Alk or 0-(CR$^{111}_2$-CR$^{III}_2$-0)y-Alk, where y=2-20, R$^{III}$, independently of one another, are H or an alkyl group, and Alk is a branched or straight-chain, saturated or unsaturated, aliphatic, aromatic or mixed aliphatic/aromatic monovalent C$_1$-C$_{20}$-hydrocarbon group,
R" is a branched or straight-chain, saturated or unsaturated, aliphatic, aromatic or mixed aliphatic/aromatic divalent C$_1$-C30-hydrocarbon group which is optionally substituted by F, C$_1$, Br, I, HS, NH$_2$ or NHR',
X=S if n=2 and m is an average sulphur chain length of from 1.5 to 4.5, and
x=SH if n=1 and m=1,
by reacting a (haloorganyl)alkoxysilane of the formula 11

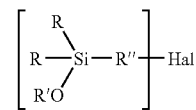

in which R, R' and R" have the above-mentioned meanings and Hal is chlorine, bromine, fluorine or iodine,
in a reaction with a sulphurization reagent selected from the group consisting of alkali metal hydrogen sulphide, metal sulphide Me$_2$S, metal polysulphide Me$_2$Sg and any desired combinations thereof, where Me=alkali metal, NH$_4$ or (alkaline earth metal)$_{1/2}$, and g=1.5-8.0, and optionally additionally with sulphur and/or with H$_2$S in alcohol, characterized in that the Me$_2$S or Me$_2$S$_g$ contains more than 10% by weight of water and the alkali metal hydrogen sulphide contains more than 3% by weight of water.

2. Process for the preparation of an organosilane according to claim 1, further comprising adding an additive before, during or after the reaction.

3. Process for the preparation of an organosilane wherein according to claim 2, the additive is a non-alcoholic solvent, polar, protic, aprotic, basic or acidic additive.

4. Process for the preparation of an organosilane according to claim 1, further comprising removing a solvent/water mixture from crude product suspension and separating off the resulting organosilane of the formula I from solid.

5. Process for the preparation of an organosilane according to claim 3, further comprising removing a solvent/water mixture from crude product suspension and separating off the resulting organosilane of the formula I from solid.

6. Process for the preparation of an organosilane according to claim 1, further comprising removing solvent from a crude product suspension, mixing the resulting mixture containing the organosilane of the formula I and solid Me(Hal) with water containing at least one buffer, and separating phases that form thereby.

7. Process for the preparation of an organosilane according to claim 1, wherein an alkali metal hydrogen sulphide is used as the water-containing sulphurization reagent in the case of organosilanes of the formula I where X=SH, m=1 and n=1.

8. Process for the preparation of an organosilane according to claim 1, wherein $Me_2S$ and sulphur are used as the water-containing sulphurization reagent in the case of organosilanes of the formula I where X=S and m=3.5-4.5.

9. Process for the preparation of an organosilane according to claim 1, wherein alkali metal hydrogen sulphides, $Me_2S$, $Me_2S_g$, and any desired combinations thereof, and optionally additionally sulphur and/or $H_2S$, are used as water-containing sulphurization reagents in the case of organosilanes of the formula I where X=S and m=1.5-4.5, and wherein the reaction is carried out in a closed vessel in the absence of air.

* * * * *